United States Patent
Sones et al.

(10) Patent No.: US 7,667,836 B2
(45) Date of Patent: *Feb. 23, 2010

(54) APPARATUS AND METHODS FOR CONTAINER INSPECTION

(75) Inventors: Richard A. Sones, Cleveland Heights, OH (US); Carl E. Sebeny, Cuyahoga Falls, OH (US); Brian M. Baird, Mantua, OH (US); Michael A. Kress, Uniontown, OH (US); Michael L. Kress, Uniontown, OH (US)

(73) Assignee: Applied Vision Company, LLC, Cuyahoga Falls, OH (US)

( * ) Notice: Subject to any disclaimer, the term of this patent is extended or adjusted under 35 U.S.C. 154(b) by 337 days.

This patent is subject to a terminal disclaimer.

(21) Appl. No.: 11/753,031

(22) Filed: May 24, 2007

(65) Prior Publication Data

US 2008/0291439 A1    Nov. 27, 2008

(51) Int. Cl.
*G01N 21/00* (2006.01)
(52) U.S. Cl. .................. 356/240.1; 356/402
(58) Field of Classification Search .............. 356/240.1, 356/402; 382/141, 152
See application file for complete search history.

(56) References Cited

U.S. PATENT DOCUMENTS

| | | | |
|---|---|---|---|
| 4,882,498 A | 11/1989 | Cochran et al. | |
| 4,972,093 A | 11/1990 | Cochran et al. | |
| 5,051,825 A | 9/1991 | Cochran et al. | |
| 5,072,127 A | 12/1991 | Cochran et al. | |
| 5,172,005 A | 12/1992 | Cochran et al. | |
| 5,331,151 A | 7/1994 | Cochran et al. | |
| 5,365,084 A | 11/1994 | Cochran et al. | |
| 5,440,385 A | 8/1995 | Fein et al. | |
| 5,451,773 A | 9/1995 | Triner et al. | |
| 5,591,462 A | 1/1997 | Darling et al. | |
| 5,911,003 A | 6/1999 | Sones | |
| 5,936,353 A | 8/1999 | Triner et al. | |
| 5,941,111 A | 8/1999 | Skala et al. | |
| 6,122,048 A | 9/2000 | Cochran et al. | |
| 6,872,895 B2 | 3/2005 | Cochran et al. | |
| 6,878,316 B1 | 4/2005 | Cochran et al. | |
| 6,894,775 B1 | 5/2005 | Cech | |
| 6,967,716 B1 | 11/2005 | Cochran et al. | |
| 2008/0292178 A1* | 11/2008 | Sones et al. .................. 382/152 |

OTHER PUBLICATIONS

Hossfeld, Michael et al.; Machine vision detects conterfeit coins; Laser Focus World, www.laserfocusworld.com; Jun. 2003; pp. 99-102.
Hosford, William F. et al.; The Aluminum Beverage Can; Scientific American; Sep. 1994; pp. 48-53.
Holman, Printz; Defect detector; The Canmaker; September; Sayers Publishing Group 2006; p. 31.

* cited by examiner

*Primary Examiner*—Roy Punnoose
(74) *Attorney, Agent, or Firm*—Hahn Loeser & Parks LLP

(57) ABSTRACT

Apparatus, systems, and methods to recognize features on bottom surfaces of metal containers on a metal container production line, detect defects in the metal containers, and correlate the defects to specific production equipment of the metal container production line, based in part on the recognized features. The system includes imaging apparatus, programmable processing devices, and controllers. The methods include imaging techniques and estimation techniques.

32 Claims, 15 Drawing Sheets

APPARATUS AND METHODS FOR CONTAINER INSPECTION

TECHNICAL FIELD

Certain embodiments of the present invention relate to inspection systems. More particularly, certain embodiments of the present invention relate to apparatus, systems, and methods for correlating detected defects in metal containers to specific production equipment on a metal container production line.

BACKGROUND

Metal containers are produced on metal container production lines at high speeds of, for example, 2000 containers per minute. The bodies of metal containers such as, for example, aluminum beverage cans, are formed by machines called "bodymakers". A bodymaker machine may perform, for example, stretching of the aluminum to create the straight sides and bottom of the metal container. At a typical metal container manufacturing plant, multiple bodymakers (e.g., 20) may feed into a single production line. The containers are processed as they move down the production line.

One process step is to spray-coat the inside of the containers. For example, there may typically be about 8 spray guns or sprayers on a production line. Each container is coated by one spray gun. The spray-coat helps protect the inside of the containers from the material (e.g., liquid) with which the container is eventually filled.

Another process step is to "neck" the containers. There may typically be about 15 "necker pockets" which form the container necks. The neck of each container is formed by a single necker pocket. Necks are formed on the containers to reduce the diameter of the top portion of the container such that a lid for the container may be smaller than the overall diameter of the container.

Another process step is to apply a "rim coating" to the bottom of the container rim (i.e., the bottom-most part of the container upon which the container stands). Such a rim coating allows the containers to slide along the metal container production line more easily helping to prevent the containers from falling over.

The bottom outside portions or surfaces of metal containers are often embossed with a body maker identifier which is, for example, a numeric value identifying which bodymaker machine made the container. As a result, a defective container may be traced back to a particular bodymaker machine by looking at the bodymaker identifier.

Similarly, the bottom outside portions or surfaces of metal containers are often marked or painted with a color dot such that the particular color of a color dot indicates which spray gun coated the inside of the container. As a result, any problems with the internal spraying of a particular container may be traced back to the particular spray gun which sprayed the container.

Furthermore, the rim coating on the bottom surface rim of a container is typically invisible under normal lighting conditions but is sensitive to ultraviolet light. That is, when the coated rim is illuminated with ultraviolet (UV) light, the rim will give off, for example, a blue color hue. As a result, the rim may be inspected under UV light to determine if the rim was properly coated.

Tracing back any particular metal container to a particular bodymaker machine, spray gun, rim coating machine may be done manually, after a defective container has been bumped off the production line. Such manual off-line tracing back is slow and inefficient and does not allow developing production problems to be identified quickly before too many defective containers are produced. Manually tracing back to a particular necker pocket is not typically done, if done at all.

Therefore there remains a need in the art to more easily, efficiently, and effectively trace back defective metal containers to the source equipment (e.g., bodymaker, spray gun, rim coater, necker) which produced the defect.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY

An embodiment of the present invention comprises an apparatus for imaging at least one color attribute of each of a plurality of metal containers, one at a time, as each container passes by the apparatus of a metal container production line. The apparatus includes a color camera having an optical aperture and a lens having a central optical axis and a capture angle. The lens is operationally attached to the color camera to provide light to the optical aperture of the color camera. The apparatus further includes a binary source of illumination arranged substantially circumferentially around the central optical axis of the lens. The binary source of illumination is capable of providing simultaneous illumination of substantially white light and ultraviolet light.

Another embodiment of the present invention comprises a method of recognizing at least one color attribute on a bottom surface of a metal container traveling on a metal container production line. The method includes acquiring a color image of a bottom surface of a metal container, having at least one color attribute, as the metal container passes by a color imaging apparatus on a metal container production line. The method further includes color balancing a pre-defined region-of-interest (ROI) of the color image to eliminate any unwanted color hue from the ROI and to provide a uniform brightness from metal container to metal container. The method also includes generating a distance value for each of a first set of pixels within the ROI to determine how different from each other are at least two color components of each of the first set of pixels. The method further includes associating pixels within the ROI, having a distance value greater than a pre-defined distance threshold value, with the color attribute. The method also includes generating an average color value of the associated pixels using corresponding color pixels in the color image and estimating a color of the color attribute in response to the average color value using a color discrimination tool.

These and other advantages and novel features of the present invention, as well as details of illustrated embodiments thereof, will be more fully understood from the following description and drawings.

DETAILED DESCRIPTION

Figure 1:
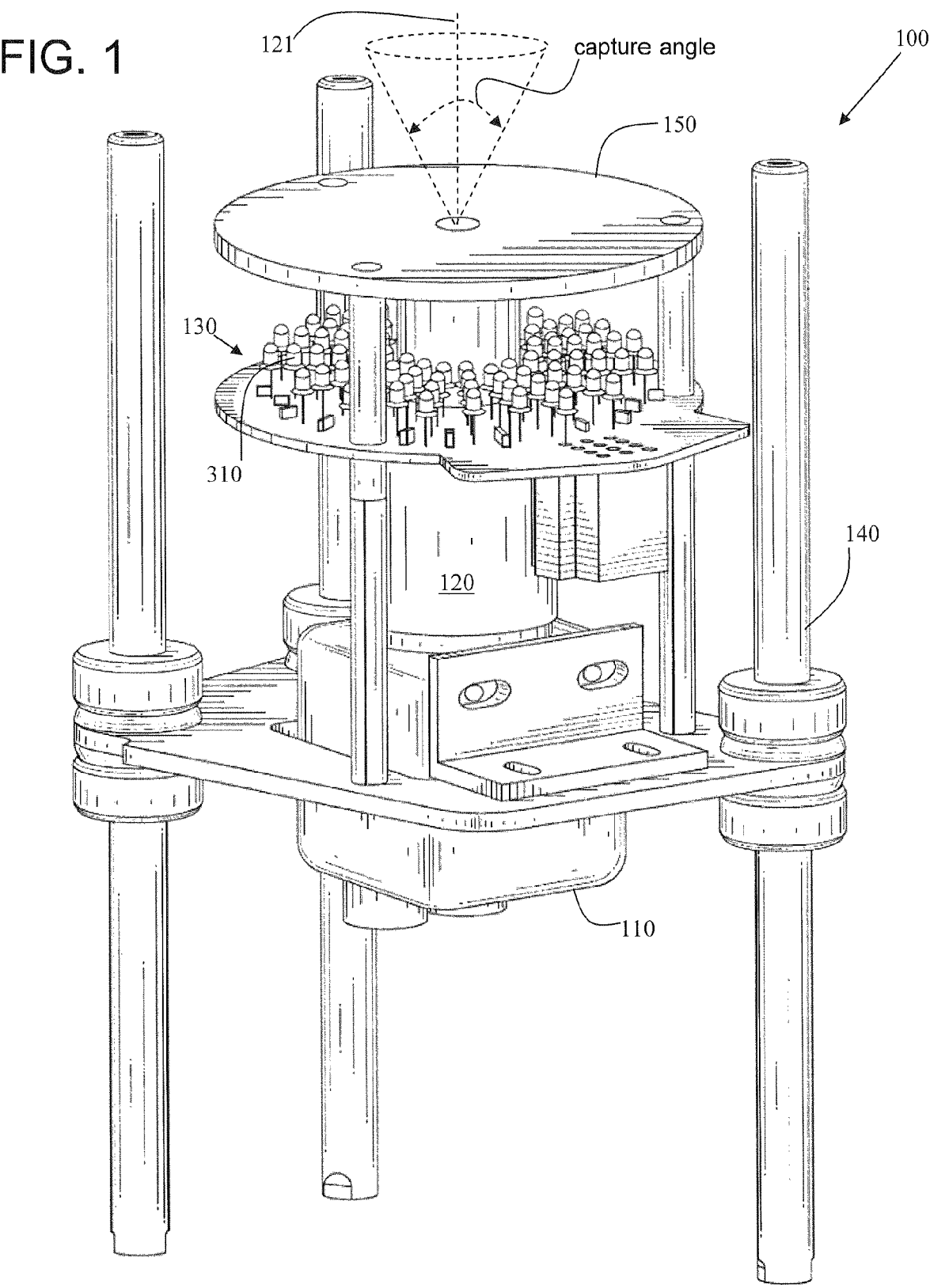
FIG. 1 is an illustration of a first embodiment of an apparatus for imaging a surface of each of a plurality of embossed containers, one at a time, as each container passes by the apparatus on a container production line.

FIG. 1 is an illustration of a first embodiment of an apparatus 100 for imaging a surface of each of a plurality of embossed metal containers, one at a time, as each container passes by the apparatus 100 on a metal container production line. The apparatus 100 includes a color camera 110 having an optical aperture, and a lens 120 having a central optical axis 121 and a capture angle. The lens 120 is operationally attached to the color camera 110 and is adapted to provide light to the optical aperture of the color camera 110. In accordance with an embodiment of the present invention, the capture angle of the lens 120 is about sixty-eight degrees. Other capture angles are possible as well. The camera 110 may comprise a digital color camera having an array of charged-coupled devices (CCDs), for example. Such digital cameras are well-known in the art. The lens 120 may include a "pin-hole" lens which is also well-known in the art.

The apparatus 100 also includes a source of illumination 130. The source of illumination 130 is arranged substantially circumferentially around the central optical axis 121 of the lens 120 and is adapted to provide simultaneous illumination in at least two substantially different colors from at least two substantially different corresponding sectors around the central optical axis 121 of the lens 120. The apparatus 100 may also be used for embossed glass containers or embossed plastic containers, as well, on respective production lines.

Figure 2:
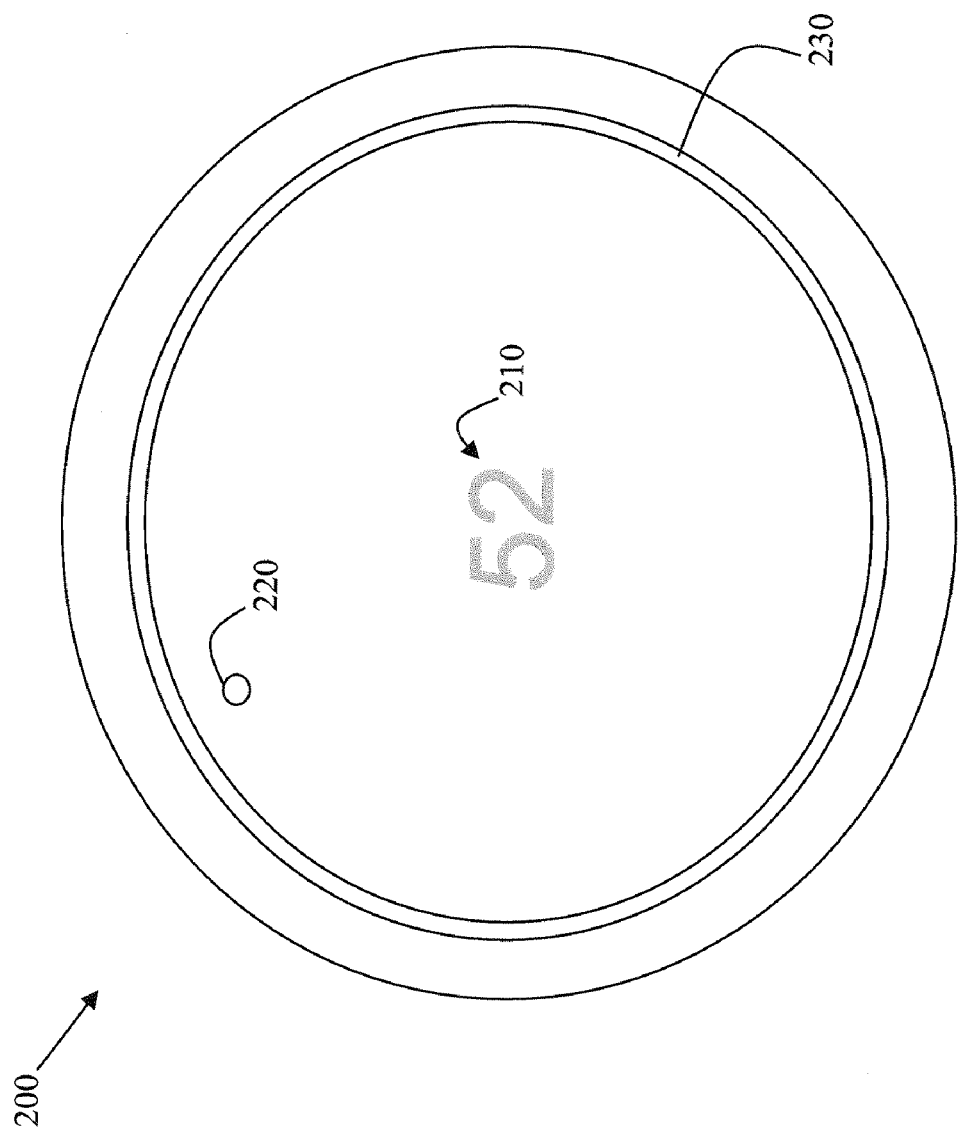
FIG. 2 is an exemplary illustration of a bottom portion of a metal container.

FIG. 2 is an exemplary illustration of a bottom portion 200 of a metal container. The bottom portion 200 includes an embossed body maker identifier 210, a color attribute such as a color dot 220, and a rim 230 coated with a substance that is sensitive to ultraviolet radiation. The embossed body maker identifier 210 may comprise any numeric code, alphabetic code, alphanumeric code, or some other character code which identifies which particular machine made the body of the metal container. In FIG. 2, the exemplary body maker identifier is the numeric code '52'. Therefore, if there is a defect or problem with the body of the metal container, the problem may be traced back to the machine that made that metal container body. The apparatus 100 is used to image the bottom portion 200 so as to allow detection and recognition of the body maker identifier 210.

The color of the color dot 220 identifies which particular sprayer sprayed the inside of the metal container. The inside of a metal container is typically sprayed with a coating to protect the inside of the metal container from reacting with, for example, the liquid material that will fill the metal container. The color dot 220 allows any particular metal container to be traced back to the sprayer which coated the inside of the metal container.

When the coated rim 230 is illuminated with ultraviolet (UV) light, the coating on the rim 230 gives off a blue color hue. The rim 230 is coated to allow the metal container to more easily slide or move along the metal container production line without falling over and possibly causing a jam. Therefore, the blue color hue may be detected to determine whether or not the rim 230 is properly coated.

Figures 3A, 3B:
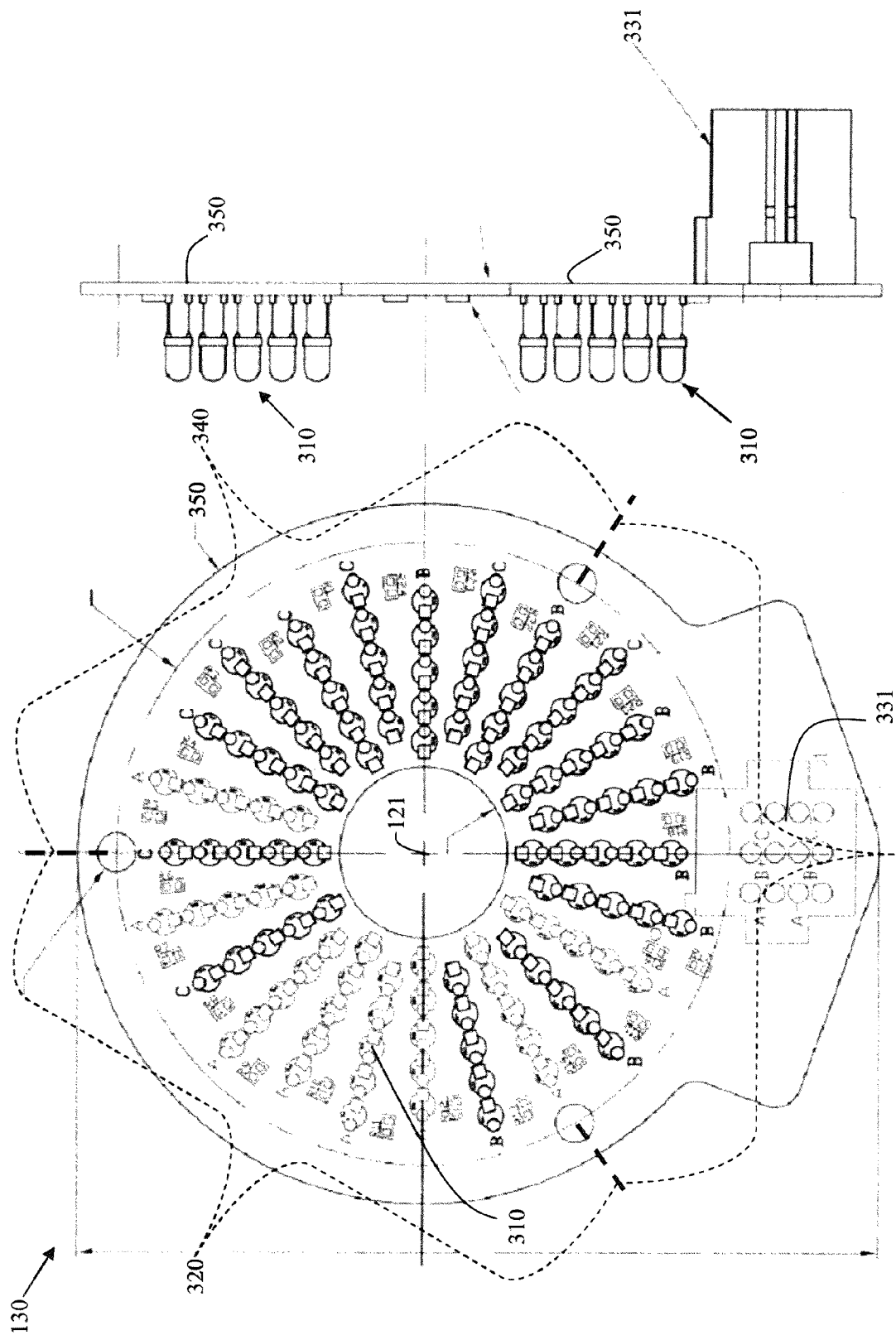
FIGS. 3A and 3B illustrate an embodiment of a source of illumination 130 used in the apparatus 100 of FIG. 1.

FIGS. 3A and 3B illustrate an embodiment of a source of illumination 130 used in the apparatus 100 of FIG. 1. FIG. 3A is a top view of the source of illumination 130 and FIG. 3B is a side view of the source of illumination 130. The source of illumination 130 includes an array of light-emitting diodes (LEDs) 310 of three substantially different colors (e.g., red (A), green (B), blue (C)). The LEDs are arranged in three substantially different corresponding sectors (320, 330, 340) on a circuit board 350 in a plane around the central optical axis 121 of the lens 120. Each of the three substantially different corresponding sectors span an angle of about 120 degrees in the plane. The source of illumination 130 also includes a connector 331 to provide electrical power and/or trigger signals to the illuminator 130.

The embossed body maker identifier on the bottom surface of a metal container is typically difficult to see under normal lighting conditions because the embossing is typically subtle. By illuminating the bottom surface of a metal container with three different colors from three different sectors or angles, a single image of the bottom surface of the metal container may be acquired by the camera 110 such that the edges of the body maker identifier 210 are enhanced by a shadowing effect. Such shadowing makes it easier to properly determine the exact code (e.g., numeric code) of the body maker identifier as is described in more detail below herein.

Figure 4:
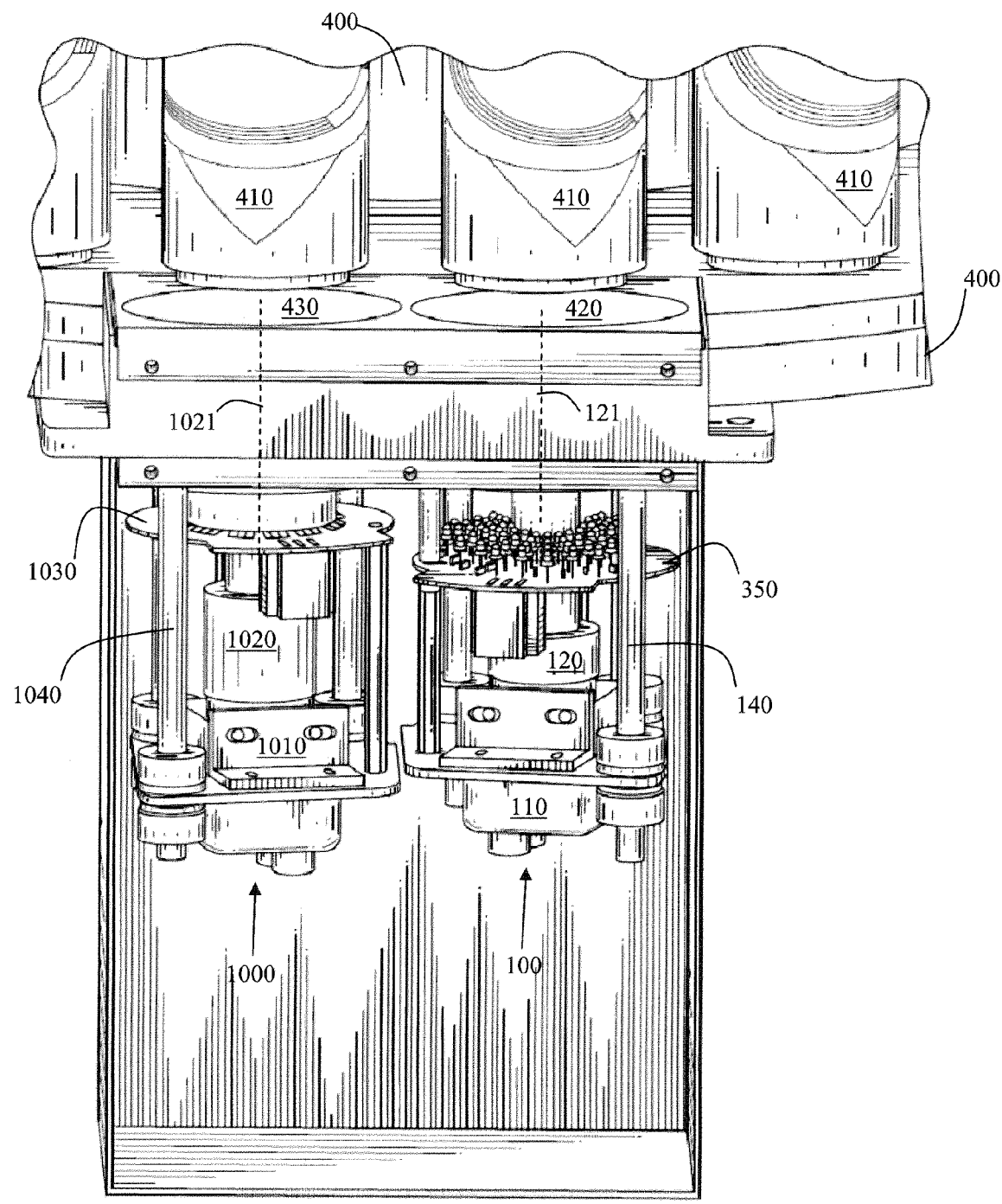
FIG. 4 is a first exemplary illustration of the apparatus of FIG. 1 mounted in a metal container production line along with an embodiment of an apparatus for imaging at least one color attribute of each of a plurality of metal containers, one at a time, as each container passes by the apparatus on a metal container production line.

FIG. 4 is a first exemplary illustration of the apparatus 100 of FIG. 1 mounted in a metal container production line along with an embodiment of an apparatus 1000 for imaging at least one color attribute (e.g., a color dot) of each of a plurality of metal containers, one at a time, as each container passes by the apparatus 1000 on a metal container production line. The apparatus 1000 is discussed in detail later herein.

The apparatus 100 and the apparatus 1000 are mounted side-by-side beneath a necker out-feeder star wheel 400 of a metal container production line. The apparatus 100 and the apparatus 1000 are mounted such that the bottom portions of metal containers 410 may be imaged as the necker out-feeder star wheel 400 rotates the metal containers (e.g., soda cans) past the apparatus 100 and the apparatus 1000. The necker out-feeder star wheel is a last star wheel of a plurality of star wheels of the metal container production line which are used to finish the neck portion of the metal containers. The star wheel typically holds each metal container in a separate pocket via vacuum or suction means and feeds the metal containers onto a conveyor belt 1380 (see FIG. 13) and toward a defect inspection system (1350 and/or 1360).

The out-feeder star wheel is the last star wheel in typically a series of interconnected star wheels which pass metal containers from one star wheel to the next to finish a next portion of the necks of the metal containers. The star wheels are typically configured such that any metal container entering a first star wheel in a particular pocket of that first star wheel (e.g., pocket number "9") will transition to the same pocket number of a next star wheel. As a result, any particular metal container is processed through the same pocket number through all of the star wheels.

The apparatus 100 includes a mounting structure 140 allowing mounting of the color camera 110, the lens 120, and the source of illumination 130 onto the necker out-feeder star wheel 400. As a result, the apparatus 100 is able to image a bottom portion 200 or surface of each of the plurality of embossed metal containers 410, one at a time, as each container passes above the apparatus 100 on the out-feeder star wheel 400. Other configurations for imaging the bottom portion of the metal containers are possible as well, which may or may not involve a necker out-feeder star wheel.

The apparatus 100 may also include a controller 1310 (see FIG. 13) operationally interfacing to the color camera 110 and/or the source of illumination 130. The controller 1310 is adapted to electronically trigger the color camera 110 and/or the source of illumination 130 to capture images. The controller 1310 may be synchronized to a rotation of the out-feeder star wheel 400 such that the color camera 110 and/or the source of illumination 130 is electronically triggered by the controller when a pocket of the out-feeder star wheel, adapted to hold one of the plurality of metal containers 410, is substantially aligned with the central optical axis 121 of the lens 120. An encoder 1340 (see FIG. 13) on the out-feeder star wheel may be used to indicate when a metal container is aligned, as will be explained in more detail later herein.

The apparatus may include an image processing device 1320 (see FIG. 13) adapted to process images acquired by the color camera 110. The image processing device 1320 and the controller 1310 may be implemented as two separate computer-based devices, for example, or as a single programmable computer-based device 1305 such as a personal computer (PC) or a programmable logic controller (PLC).

The apparatus 100 may include a diffuser window 150 located adjacent to the lens 120 and the source of illumination 130 and adapted to substantially diffuse the at least two substantially different colors from the source of illumination 130. Furthermore, the apparatus may include a substantially transparent window 420 located adjacent the lens 120 and the source of illumination 130 to protect the lens 120 and the source of illumination 130 from dirt, debris, and other materials.

Figure 5:
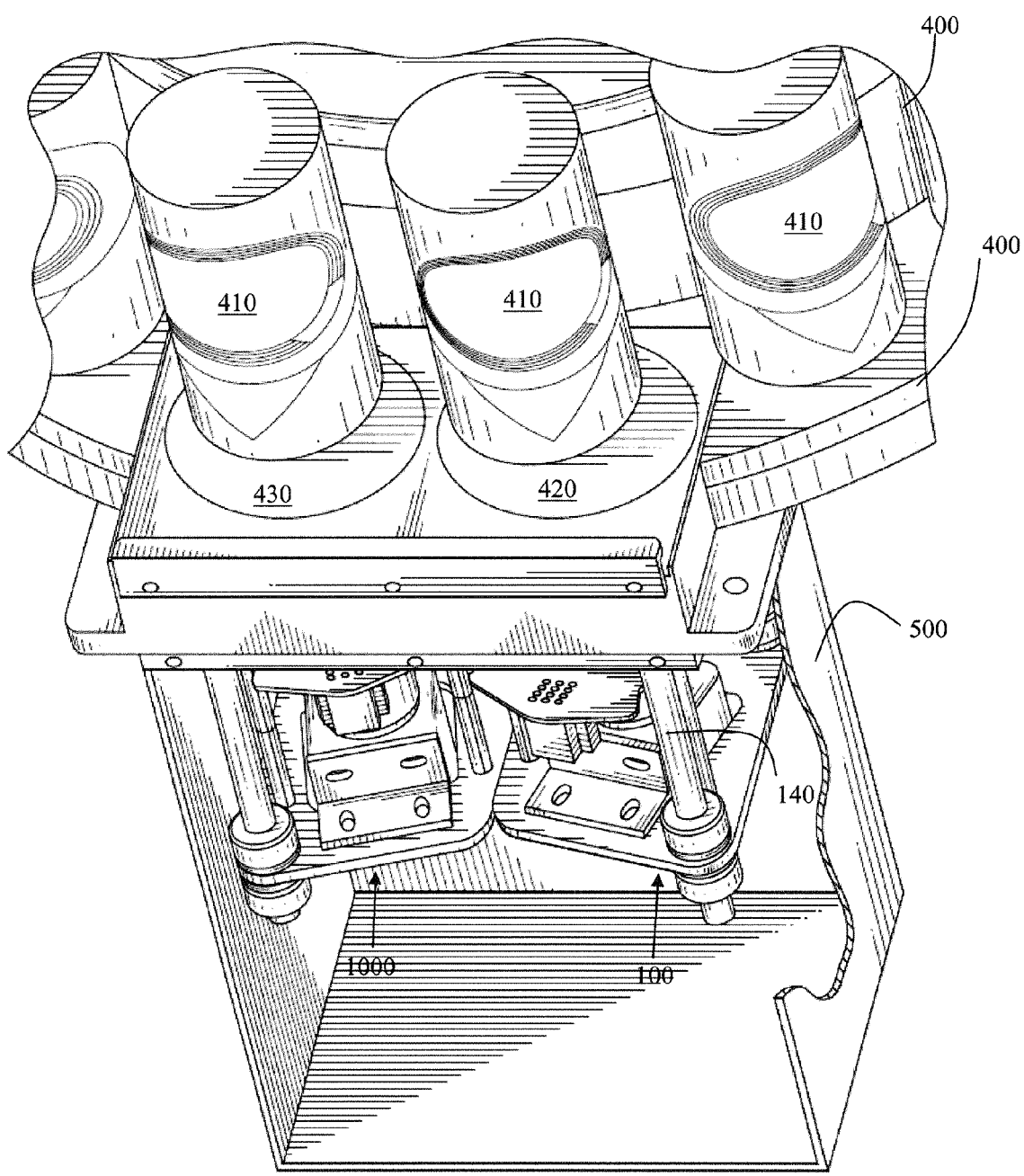
FIG. 5 is a second exemplary illustration of the apparatus of FIG. 1 mounted in a metal container production line along with an embodiment of an apparatus for imaging at least one color attribute of each of a plurality of metal containers, one at a time, as each container passes by the apparatus on a metal container production line.

FIG. 5 is a second exemplary illustration of the apparatus 100 of FIG. 1 mounted in a metal container production line along with an embodiment of an apparatus 1000 for imaging at least one color attribute of each of a plurality of metal containers, one at a time, as each container passes by the apparatus 1000 on a metal container production line. FIG. 5 provides a different perspective of the spatial relationship of the star wheel 400, the metal containers 410, the apparatus 100, and the apparatus 1000. The apparatus 100 and the apparatus 1000 may be enclosed in a housing 500 for further protection.

Figure 6:
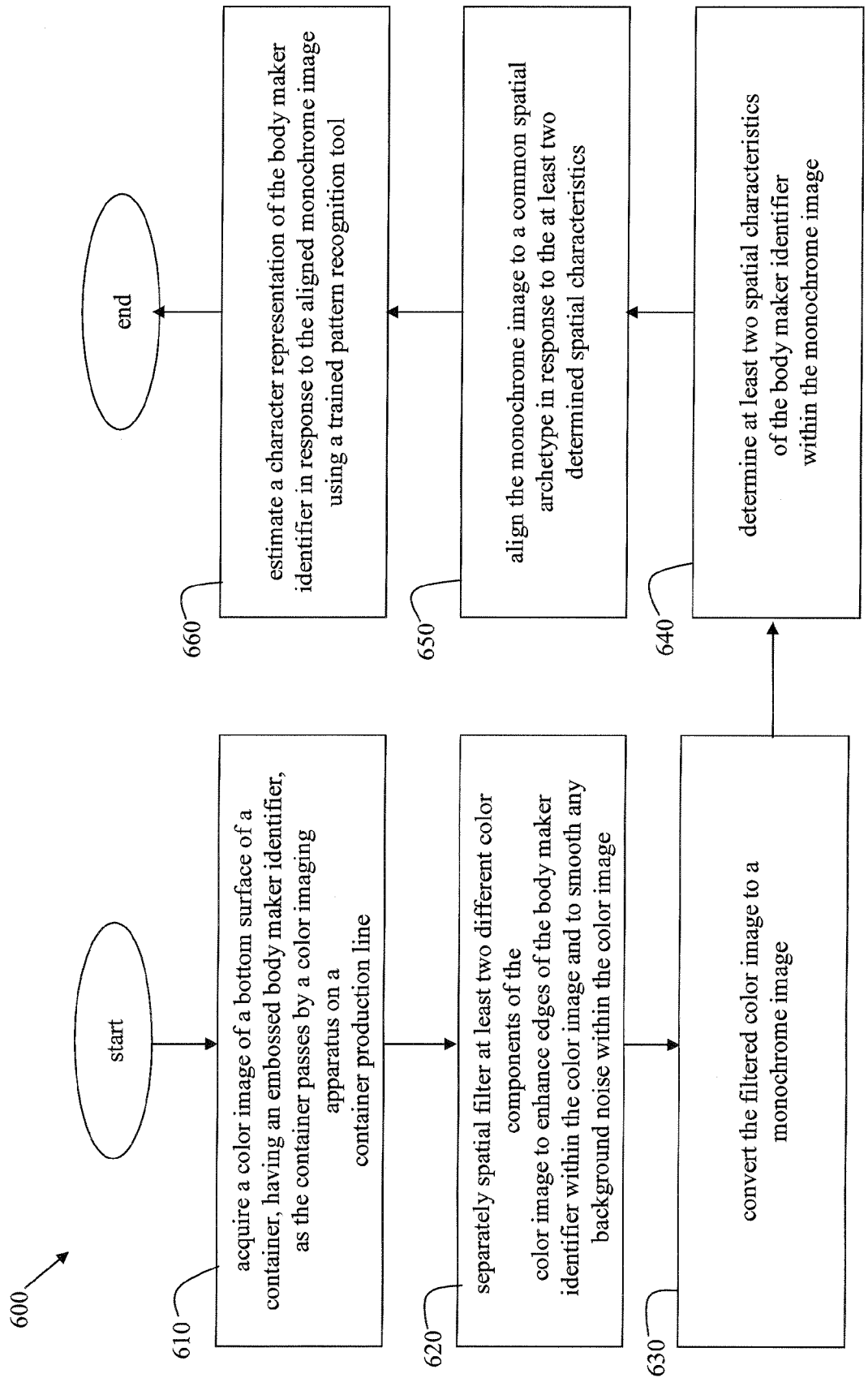
FIG. 6 is a flow chart of an embodiment of a method of recognizing an embossed body maker identifier on a bottom surface of a container traveling on a container production line using the apparatus of FIG. 1.

FIG. 6 is a flow chart of an embodiment of a method 600 of recognizing an embossed body maker identifier on a bottom surface of a metal container traveling on a metal container production line using the apparatus 100 of FIG. 1. In step 610, acquire a color image of a bottom surface of a metal container, having an embossed body maker identifier, as the metal container passes by the color imaging apparatus 100 on a metal container production line.

In step 620, separately spatial filter at least two different color components (e.g., red component, green component, blue component) of the color image to enhance edges of the body maker identifier within the color image and to smooth any background noise within the color image. The spatial filtering may include performing a high-pass filtering function for edge enhancement and a low-pass filtering function for noise smoothing.

In step 630, convert the filtered color image to a monochrome image. In step 640, determine at least two spatial characteristics of the body maker identifier within the monochrome image. In accordance with an embodiment of the present invention, determining the two spatial characteristics includes finding a minimum area rectangle that bounds the body maker identifier of the monochrome image such that a center and an angle of orientation (i.e., two spatial characteristics) of the minimum area rectangle are determined. Finding the minimum area rectangle may include converting the monochrome image (e.g., a clipped monochrome image) to a binary image of two colors and finding regions within the binary image that are connected together. The binary image of connected regions is then thresholded to eliminate the regions which are smaller than a pre-defined size from the binary image.

In step 650, align the monochrome image to a common spatial archetype in response to the at least two determined spatial characteristics. In step 660, estimate a character representation of the body maker identifier in response to the aligned monochrome image using a trained pattern recognition tool. The metal containers may be randomly oriented on the metal container production line and, therefore, the body maker identifier may be randomly oriented as well. Having the image aligned to a common spatial archetype makes it easier for the trained pattern recognition tool to correctly estimate the body maker identifier. A confidence level may be generated as part of the estimating step (e.g., 95% confident that the estimate is correct). The method 600 is performed automatically and on-line in real time as the metal container production line is manufacturing metal containers.

The method 600 may further include determining at least two spatial parameters of the imaged bottom surface in response to the acquired color image and scaling the color image in response to the determined at least two spatial parameters. Such a step may be performed after the step of converting the color image to a monochrome image. For example, the two spatial parameters may include a center location and a radius of the imaged bottom surface. Using the center and radius determined from the monochrome image allows the monochrome image to be scaled to account for differences in spatial locations (e.g., vertical displacement) from metal container to metal container. Having the image scaled to a normalized size makes it easier for the trained pattern recognition tool to correctly estimate the body maker identifier.

As the color image is acquired, the bottom surface of the metal container is illuminated with at least two substantially different colors originating from at least two substantially different sectors below the bottom surface. For example, the illuminator 130 may be used to illuminate the bottom surface of a metal container with red, green, and blue light from three substantially different sectors (320, 330, 340) at the time of image acquisition. The illuminator 130 may be triggered by the controller 1310 to aid in acquisition of the image when a metal container is substantially aligned with the optical axis 121. Alternatively, the illuminator 130 may be continuously on.

In accordance with an embodiment of the present invention, a histogram normalization function may be applied to the monochrome image to brighten the monochrome image and to provide more contrast within the monochrome image. Furthermore, a clipping function may be applied to the brightened monochrome image to make a background region around the body maker identifier a solid uniform color (e.g., black).

As will be described in more detail later herein, the estimated character representation of the body maker identifier of the metal container may be correlated to a pocket of an out-feeder star wheel 400 of the metal container production line in which the metal container is held, as well as to other features and inspection results.

The pattern recognition tool is trained from a plurality of aligned monochrome images derived from a corresponding plurality of acquired color images that have been processed through at least the filtering step 620, the converting step 630, the determining step 640, and the aligning step 650. The pattern recognition tool may comprise a trained neural network or a trained function and/or algorithm derived from an evolutionary algorithm, for example. Other types of pattern recognition tools may be possible as well. Such pattern recognition tools are well-known in the art. The training involves collecting many images having various body maker identifiers (e.g., "10", "15", "22", etc.) and telling the pattern recognition tool the correct body maker identifier number for each image. The tool then "trains up" to output a correct estimate of the body maker identifier when presented with an image having that body maker identifier.

Figure 7:
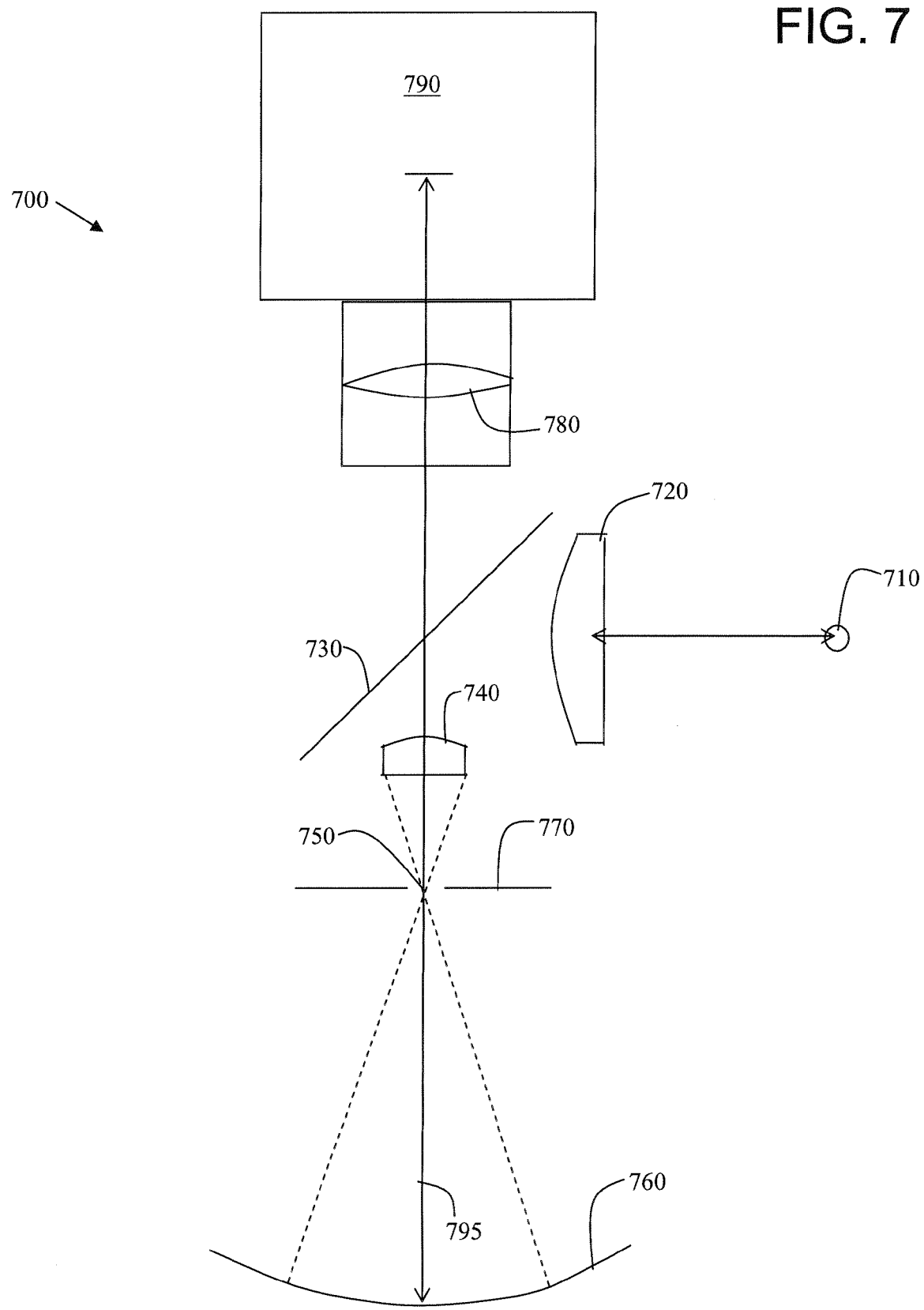
FIG. 7 is an illustration of a second embodiment of an apparatus for imaging a surface of each of a plurality of embossed metal containers, one at a time, as each container passes by the apparatus on a metal container production line.

FIG. 7 is an illustration of a second embodiment of an apparatus 700 for imaging a surface of each of a plurality of embossed metal containers, one at a time, as each container passes by the apparatus 700 on a metal container production line. The apparatus 700 includes a light source 710 (e.g., a substantially point light source such as a light-emitting diode or a light bulb). The apparatus 700 also includes a collimating lens 720 positioned to be illuminated on a first side by the light source and to output substantially parallel rays of light from a second side in response to the illumination.

The apparatus 700 further includes a beam-splitting mirror 730 positioned to first reflect the parallel rays of light received from the collimating lens 720. The apparatus includes a focusing lens 740 positioned to receive and focus the first reflected parallel rays of light forward to a focal point 750 and toward a substantially concave surface 760 of a metal container. The concave surface 760 of the metal container has an embossed portion (e.g., an embossed body maker identifier). A first portion of the focused rays of light impinge substantially perpendicularly on the substantially concave surface 760 and subsequently reflect off of the concave surface 760 back to the focal point 750 and backward through the focusing lens 740 toward the beam-splitting mirror 730. A second portion of the focused rays of light may impinge substantially on the embossed portion and subsequently reflect substantially away from the focal point 750 and the focusing lens 740. As a result, at least the edges of the embossed portion are highlighted or shadowed within a subsequently captured image. The substantially concave surface 760 acts as an optical element working in conjunction with the apparatus 700.

The apparatus 700 further includes a camera lens 780 to receive the subsequently reflected rays of light after the rays of light pass backward through the focusing lens 740 and through the beam-splitting mirror 730. The apparatus 700 also includes a camera 790 having an optical aperture positioned to capture the rays of light received by the camera lens 780. The camera 790 is adapted to generate an image of the concave surface of the metal container in response to the captured rays of light such that at least an outline of the embossed portion is substantially discernible within the generated image. The camera 790 may comprise a digital monochrome camera having an array of charged-coupled devices (CCDs), for example. Such digital cameras are well-known in the art.

As an option, the apparatus 700 may include an aperture 770 positioned substantially at the focal point 750 and adapted to help block reflected rays of light from the substantially concave surface 760 that are not perpendicular to the concave surface 760, and pass reflected rays of light from the substantially concave surface 760 that are perpendicular to the concave surface 760.

The apparatus 700 may further include a controller 1310 (see FIG. 13) operationally interfacing to the camera 790 and/or the light source 710. The controller 1310 is adapted to electronically trigger the camera 790 and/or the light source 710 to capture rays of light received by the camera lens 780. The controller 1310 may be synchronized to a rotation of the out-feeder star wheel 400 such that the camera 790 and/or the light source 710 is electronically triggered by the controller when a pocket of the out-feeder star wheel, adapted to hold one of the plurality of metal containers 410, is substantially aligned with a central optical axis 795 of the apparatus 700.

The apparatus 700 may include an image processing device 1320 (see FIG. 13) adapted to process images acquired by the camera 790. The processing device 1320 and the controller 1310 may be implemented as two separate computer-based devices, for example, or as a single programmable computer-based device 1305 such as a personal computer (PC) or a PLC.

The apparatus 700 may include a mounting structure 140 (similar to that illustrated for the first embodiment in FIG. 1 and FIG. 4) adapted to allow mounting of the light source 710, the collimating lens 720, the beam-splitter mirror 730, the focusing lens 740, the camera lens 780, and the camera 790 onto an out-feeder star wheel of the metal container production line. As a result, the apparatus 700 is capable of imaging a bottom surface of each of a plurality of embossed metal containers, one at a time, as each container passes above the apparatus on the out-feeder star wheel.

Figure 8:
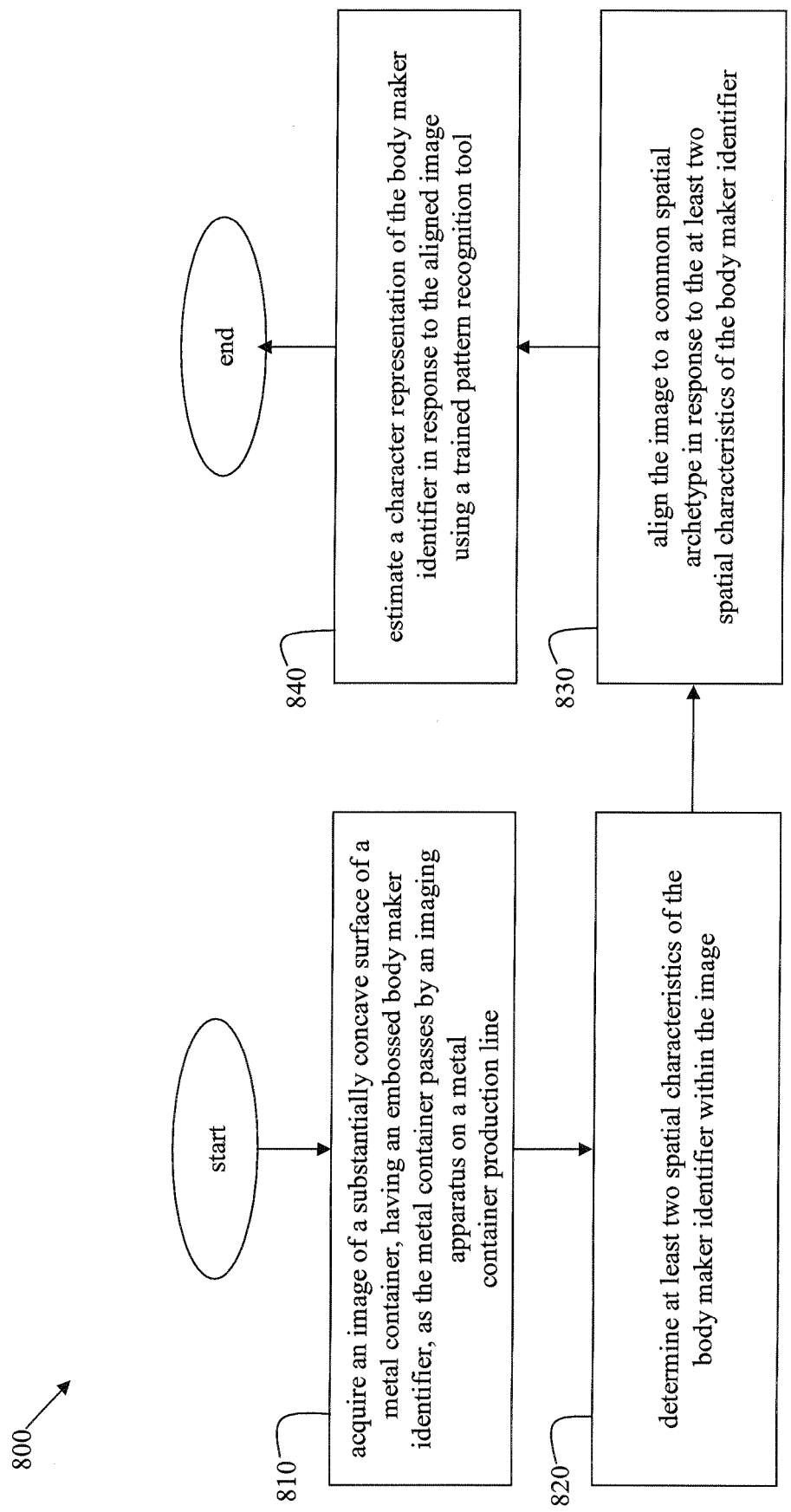
FIG. 8 is a flow chart of an embodiment of a method of recognizing an embossed body maker identifier on a bottom surface of a metal container traveling on a metal container production line using the apparatus of FIG. 7.

FIG. 8 is a flow chart of an embodiment of a method 800 of recognizing an embossed body maker identifier on a bottom surface of a metal container traveling on a metal container production line using the apparatus 700 of FIG. 7. In step 810, acquire an image of a substantially concave surface of a metal container, having an embossed body maker identifier, as the metal container passes by an imaging apparatus on a metal container production line. In step 820, determine at least two spatial characteristics of the body maker identifier within the image. In accordance with an embodiment of the present invention, determining the two spatial characteristics includes finding a minimum area rectangle that bounds the body maker identifier of the image such that a center and an angle of orientation (i.e., two spatial characteristics) of the minimum area rectangle are determined. Finding the minimum area rectangle may include converting the image (e.g., a clipped image) to a binary image of two colors and finding regions within the binary image that are connected together. The binary image of connected regions is then thresholded to eliminate the regions which are smaller than a pre-defined size from the binary image.

In step 830, align the image to a common spatial archetype in response to the at least two spatial characteristics of the body maker identifier. In step 840, estimate a character representation of the body maker identifier in response to the aligned image using a trained pattern recognition tool. Having the image aligned to a common spatial archetype makes it easier for the trained pattern recognition tool to correctly estimate the body maker identifier. Again, a confidence level may be generated as part of the estimating step. The method 800 is performed automatically and on-line in real time as the metal container production line is manufacturing metal containers.

The method 800 may further include determining at least two spatial parameters of the imaged concave surface in response to the acquired image and scaling the acquired image in response to the determined at least two spatial parameters. For example, the two spatial parameters may include a center location and a radius of the imaged bottom surface. Using the center and radius determined from the image allows the image to be scaled to account for differences in spatial locations (e.g., vertical displacement) from metal container to metal container. Having the image scaled to a normalized size makes it easier for the trained pattern recognition tool to correctly estimate the body maker identifier.

The method 800 further comprises illuminating the substantially concave surface of the metal container with rays of light being substantially perpendicular to the substantially concave surface as described above with respect to FIG. 7. As the image is acquired, the concave surface of the metal container is illuminated via a point light source. For example, the light source 710 may be used to illuminate the concave surface of a metal container with white light via the optical path described above for FIG. 7 at the time of image acquisition. The light source 710 may be triggered by the controller 1310 to aid in acquisition of the image when a metal container is substantially aligned with the optical axis 795. Alternatively, the light source 710 may be continuously on.

The acquired image may be spatially filtered to enhance edges of the body maker identifier within the image and to smooth any background noise within the image. The spatial filtering may include performing a high-pass filtering function for edge enhancement and a low-pass filtering function for noise smoothing. Such spatial filtering is performed at least before the estimating step 840.

In accordance with an embodiment of the present invention, a histogram normalization function may be applied to the image to brighten the image and to provide more contrast within the image. Furthermore, a clipping function may be applied to the brightened image to make a background region around the body maker identifier a solid uniform color (e.g., black).

As will be described in more detail later herein, the estimated character representation of the body maker identifier of the metal container may be correlated to a pocket of an outfeeder star wheel 400 of the metal container production line in which the metal container is held, as well as to other features and inspection results.

The pattern recognition tool is trained from a plurality of aligned images derived from a corresponding plurality of acquired images that have been processed through at least the determining step 820, and the aligning step 830. The pattern recognition tool may comprise a trained neural network or a trained function and/or algorithm derived from an evolutionary algorithm, for example. Other types of pattern recognition tools may be possible as well. Such pattern recognition tools are well-known in the art.

Figure 9:
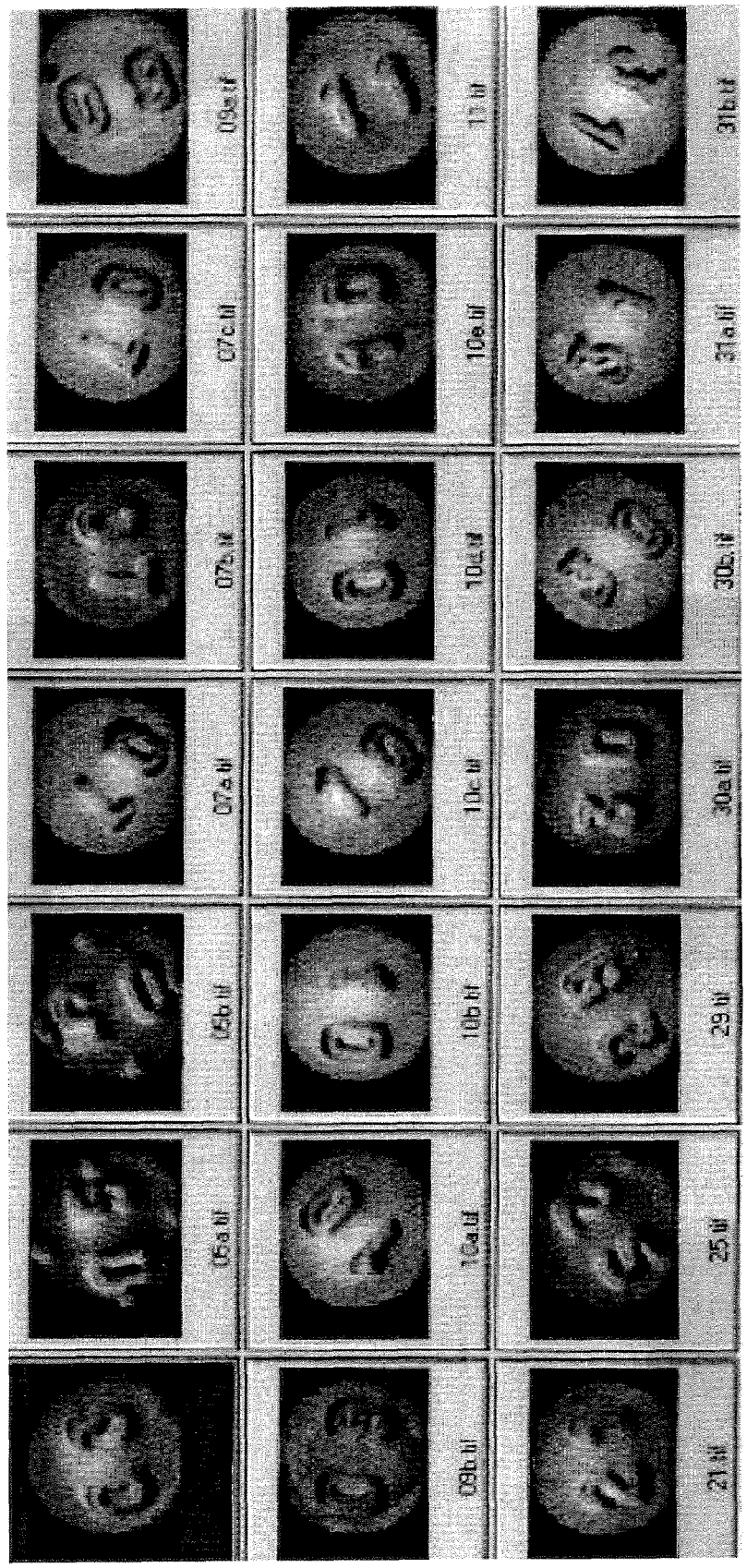
FIG. 9 illustrates a plurality of images captured by the apparatus of FIG. 7.

FIG. 9 illustrates a plurality of images 900 captured by the apparatus of FIG. 7. The images correspond to the bottom concave surfaces of different metal containers. Each image shows an embossed body maker identifier (numbers in this example) having shadowed or high-lighted edges due to the effect produced by the optics of the apparatus 700. The body maker identifier numbers seem to "jump out" of the image in a three-dimensional sense, making it easier to estimate the actual number (e.g., 03, 05, 07, 08, 10, 11, 21, 25, 29, 30, 31, etc.). Each unique body maker identifier number corresponds to a different body maker machine within a metal container production line.

Figure 10:
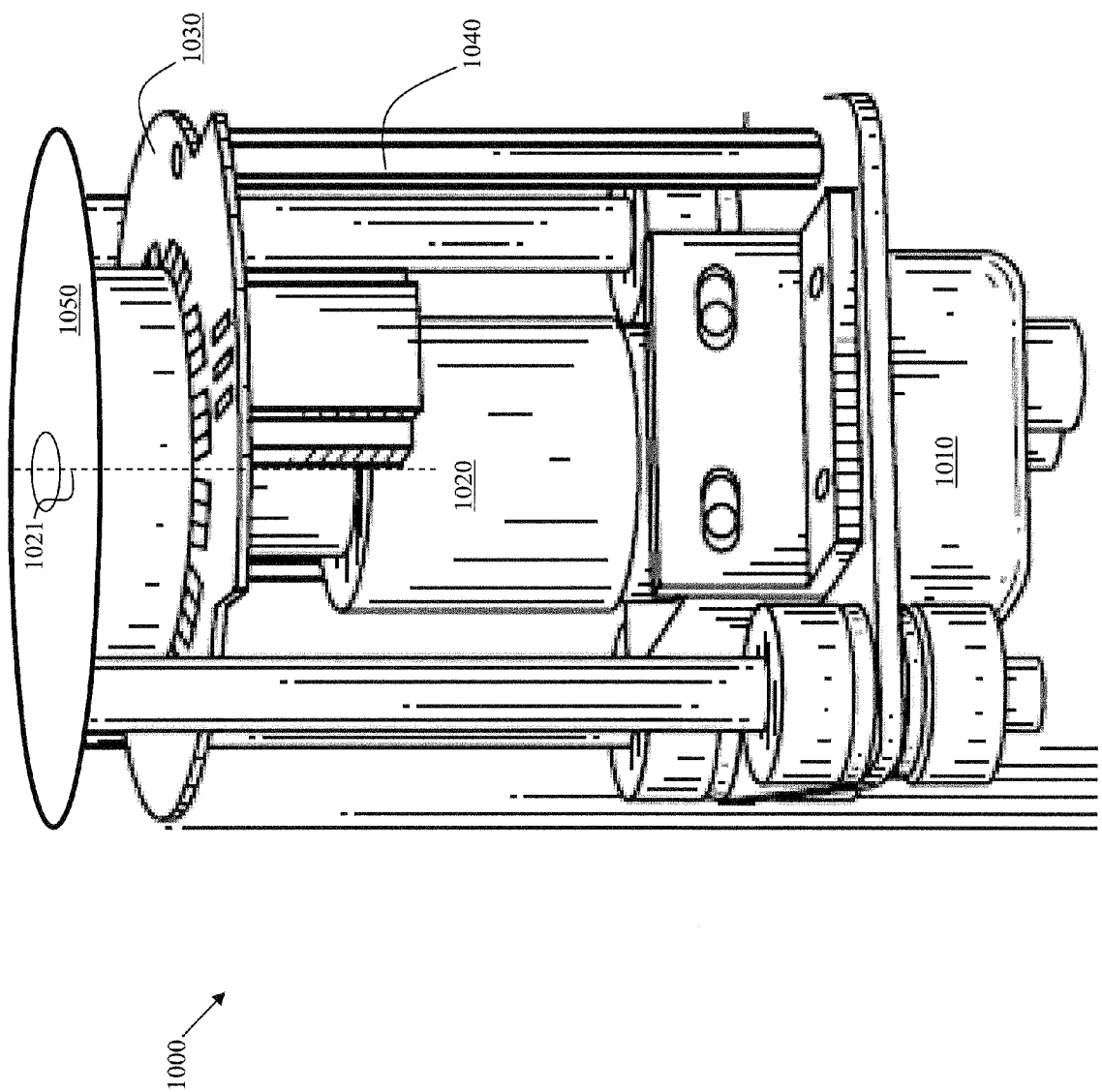
FIG. 10 illustrates an embodiment of the apparatus for imaging at least one color attribute of each of a plurality of metal containers, one at a time, as each container passes by the apparatus on a metal container production line.

FIG. 10 illustrates an embodiment of the apparatus 1000 for imaging at least one color attribute (e.g., a color dot) of each of a plurality of metal containers, one at a time, as each container passes by the apparatus 1000 on a metal container production line. The apparatus 1000 includes a color camera 1010 having an optical aperture, and a lens 1020 having a central optical axis 1021 and a capture angle. The lens 1020 is operationally attached to the color camera 1010 to provide light to the optical aperture of the color camera 1010. In accordance with an embodiment of the present invention, the capture angle of the lens 1020 is about sixty-eight degrees. Other capture angles are possible as well. The camera 1010 may comprise a digital color camera having an array of charged-coupled devices (CCDs), for example. Such digital cameras are well-known in the art. The lens 1020 may include a "pin-hole" lens which is also well-known in the art. The apparatus 1000 further includes a binary source of illumination 1030 arranged circumferentially around the central optical axis 1021 of the lens 1020. The binary source of illumination 1030 is capable of providing simultaneous illumination of substantially white light and ultraviolet light.

Figures 11A, 11B:
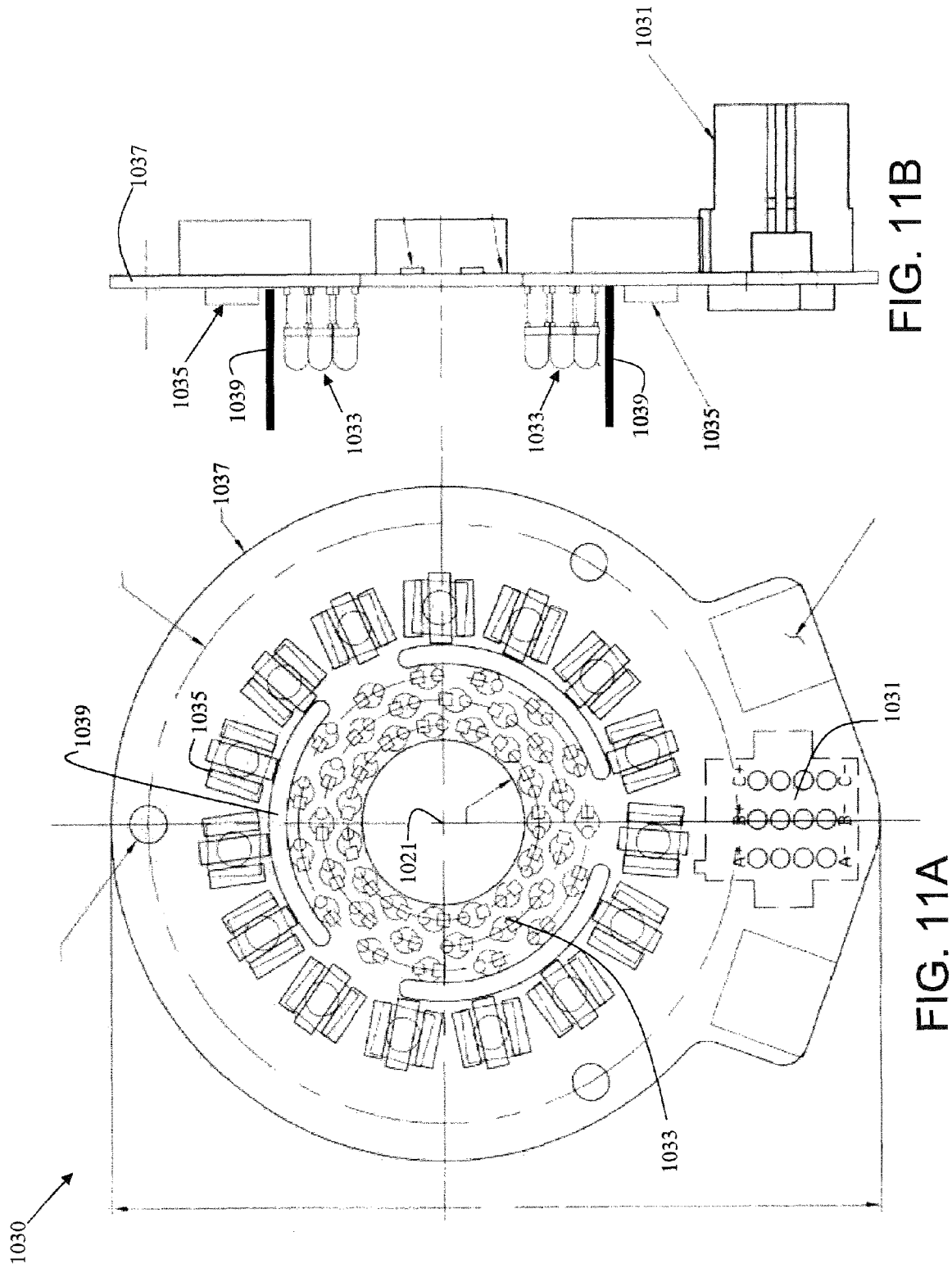
FIGS. 11A and 11B illustrate an embodiment of a binary source of illumination used in the apparatus of FIG. 10.

FIGS. 11A and 11B illustrate an embodiment of a binary source of illumination 1030 used in the apparatus 1000 of FIG. 10. FIG. 11A is a top view of the binary source of illumination 1030 and FIG. 11B is a side view of the source of illumination 1030. The binary source of illumination 1030 includes an array of substantially white light emitting diodes (LEDs) 1033 and ultraviolet LEDs 1035 arranged in a plane around the central optical axis 1021. In accordance with an embodiment of the present invention, the array of substantially white LEDs 1033 are arranged in three concentric rings around the central optical axis 1021. The ultraviolet LEDs 1035 are substantially arranged in a concentric ring around the white LEDs 1033. The binary source of illumination 1030 also includes a connector 1031 to provide electrical power and/or trigger signals to the illuminator 1030.

The LEDs 1033 and LEDs 1035 are mounted on a circuit board 1037. The binary source of illumination 1030 also includes a substantially tubular separator 1039 positioned concentrically between the white LEDs 1033 and the ultraviolet LEDs 1035. The inner surface of the separator 1039 faces the white LEDs and is substantially white. The outer surface of the separator 1039 faces the ultraviolet LEDs and is substantially silver. The separator 1039 helps to keep the white light illumination separate from the ultraviolet illumination and direct the illuminations upward toward the bottom surface of the metal container to be imaged. The white light illumination is used for illuminating a color feature 220 (e.g., a color dot) on the bottom surface of the metal container. The ultraviolet illumination is used for illuminating the coated rim 230 on the bottom surface of the metal container. The separator 1039 helps prevent white light from the white LEDs 1033 from swamping the coated rim 230 with white light.

The apparatus 1000 may further include a controller 1310 (see FIG. 13) operationally interfacing to the camera 1010 and/or the binary light source 1030. The controller 1310 is adapted to electronically trigger the camera 1010 and/or the binary light source 1030 to capture rays of light received by the camera lens 1020. The controller 1310 may be synchronized to a rotation of the out-feeder star wheel 400 such that the camera 1010 and/or the binary light source 1030 is electronically triggered by the controller when a pocket of the out-feeder star wheel, adapted to hold one of the plurality of metal containers 410, is substantially aligned with a central optical axis 1021 of the apparatus 1000.

The apparatus 1000 may include an image processing device 1320 (see FIG. 13) adapted to process images acquired by the camera 1010. The image processing device 1320 and the controller 1310 may be implemented as two separate computer-based devices, for example, or as a single programmable computer-based device 1305 such as a personal computer (PC) or PLC.

The apparatus 1000 may include a mounting structure 1040 (similar to that illustrated for the first embodiment in FIG. 1 and FIG. 4) adapted to allow mounting of the binary light source 1030, the lens 1020, and the camera 1010 onto an out-feeder star wheel of the metal container production line. As a result, the apparatus 1000 is capable of imaging a bottom surface of each of a plurality of metal containers, one at a time, as each container passes above the apparatus 1000 on the out-feeder star wheel. Just as for the first embodiment shown in FIG. 1 and FIG. 4, the apparatus 1000 may include a substantially transparent window 430 and a diffuser window 1050 serving similar purposes.

Figure 12:
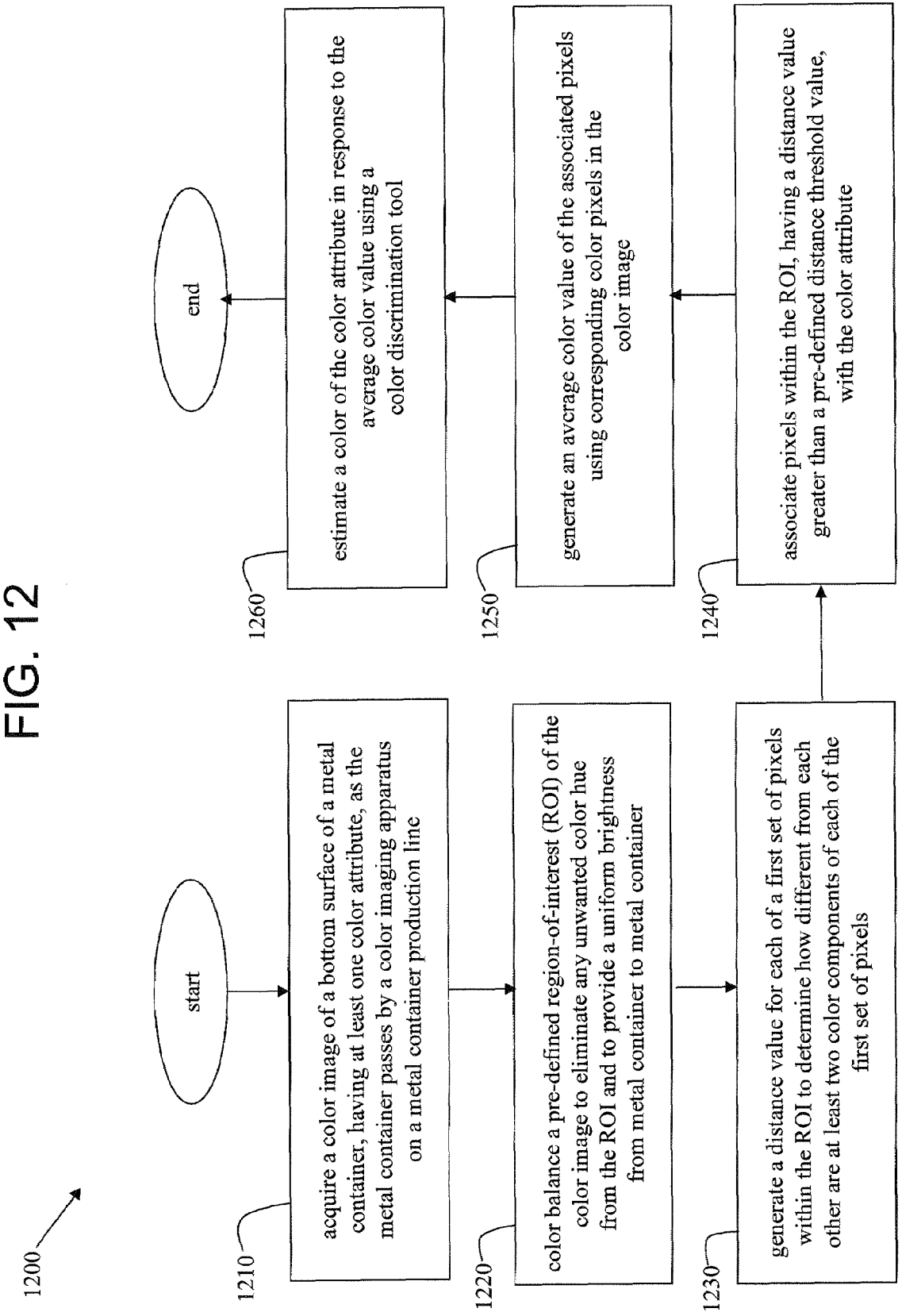
FIG. 12 is a flow chart of an embodiment of a method of recognizing at least one color attribute on a bottom surface of a metal container traveling on a metal container production line using the apparatus of FIG. 10.

FIG. 12 is a flow chart of an embodiment of a method 1200 of recognizing at least one color attribute on a bottom surface of a metal container traveling on a metal container production line using the apparatus 1000 of FIG. 10. In step 1210, acquire a color image of a bottom surface of a metal container, having at least one color attribute, as the metal container passes by a color imaging apparatus 1000 on a metal container production line. In step 1220, color balance a pre-defined region-of-interest (ROI) of the color image to eliminate any unwanted color hue from the ROI and to provide a uniform brightness from metal container to metal container. In step 1230, generate a distance value for each of a first set of pixels within the ROI to determine how different from each other are at least two color components of each of the first set of pixels. In step 1240, associate pixels within the ROI, having a distance value greater than a pre-defined distance threshold value, with the color attribute. In step 1250, generate an average color value of the associated pixels using corresponding color pixels in the color image. In step 1260, estimate a color of the color attribute in response to the average color value using a color discrimination tool. The method 1200 is performed automatically and on-line in real time as the metal container production line is manufacturing metal containers.

As part of acquiring the color image in step 1210, the method includes simultaneously illuminating a first portion of the bottom surface of the metal container with substantially white light and a second portion of the bottom surface with ultraviolet light.

The color discrimination tool is trained from a plurality of estimated color attributes derived from a corresponding plurality of acquired color images that have been processed through at least the color balancing step 1220, the first generating step 1230, the associating step 1240, and the second generating step 1250. In accordance with an embodiment of the present invention, the color attribute may include a mark of color (e.g., a color dot 220) painted or sprayed on the bottom surface of the metal container.

The step 1220 of color balancing includes measuring average values of red, green, and blue color components of pixels within the ROI. The red, green, and blue color components of each pixel within the ROI are then scaled in response to the measured average values of red, green, and blue color components such that an average of each of the red, green, and blue color components of pixels within the ROI become equal to each other.

In accordance with an embodiment of the present invention, the distance value for any pixel having the color components of red R, green G, and blue B is a function of a quantity defined as $[(R-G)^2+(R-B)^2+(G-B)^2]$. Furthermore, the method 1200 may include comparing a number N of the associated pixels with a threshold value V such that the associated pixels are not considered to correspond to the color attribute if the number N of the associated pixels is less than the threshold value V.

In accordance with an embodiment of the present invention, any pixel having each of a red color component R, a green color component G, and a blue color component B being less than a threshold value BL may be flagged as being black.

The method 1200 may further include determining a number NB of a second set of pixels within the color image that are outside of the pre-defined ROI and having a blue color component value that is greater than a pre-defined blue threshold value. The method further includes comparing the number NB to a pre-defined rim coat test threshold value RCT. A "fail" condition is generated if the number NB is less than the rim coat test threshold value RCT, indicating that the rim 230 of the metal container is not adequately coated with the UV-sensitive coating material in order to help the metal containers slide more easily on the production line.

The method 1200 may further include determining at least two spatial parameters of the imaged bottom surface in response to the acquired color image and scaling the acquired color image in response to the determined at least two spatial parameters. The at least two spatial parameters may include a center location and a radius of the imaged bottom surface. In accordance with an embodiment of the present invention, the step of determining the at least two spatial parameters includes first converting the acquired color image to a monochrome image.

The method 1200 further includes associating the metal container with a particular sprayer or spray gun in response to the estimated color. Associating the metal container with a particular spray gun in response to the estimated color may include determining which cluster in a color space, of a plurality of clusters in the color space corresponding to a plurality of spray guns, is closest in the color space, to the estimated color. In accordance with an embodiment of the present invention, the color space includes a domain of color hue and color saturation. Each cluster of the plurality of clusters includes a pre-defined centroid in the color space derived from estimated colors corresponding to the spray guns.

Furthermore, the method may include correlating the estimated color of the color attribute to a pocket of an out-feeder star wheel of the metal container production line as well as to other features and inspection results. The out-feeder star wheel is adapted to hold the metal container via, for example, a vacuum or suction technique.

Figure 13:
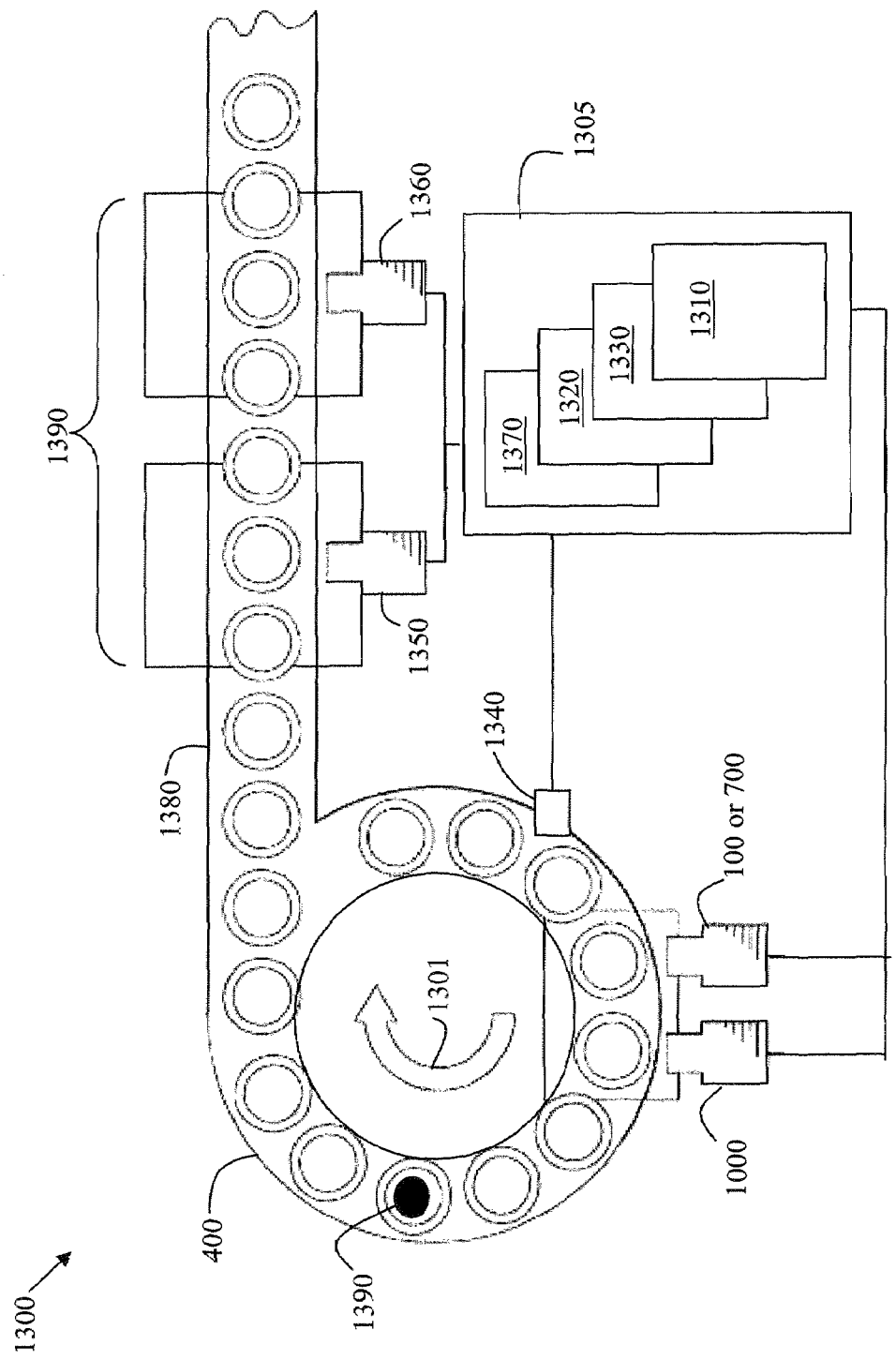
FIG. 13 is an exemplary illustration of an embodiment of a system for associating a defective metal container produced on a metal container production line with particular production equipment of the metal container production line.

FIG. 13 is an exemplary illustration of an embodiment of a system 1300 for associating a defective metal container produced on a metal container production line with particular production equipment of the metal container production line. In accordance with an embodiment of the present invention, metal containers enter the pockets of a necker out-feeder star wheel 400 and transition to a conveyor 1380 toward an inspection section 1390 of the metal container production line in series (one after another in adjacent positions). In other embodiments, the necker out-feeder star wheel may not be present.

The system 1300 includes at least one feature-detecting imaging apparatus (e.g., 100 or 700, and/or 1000) mounted proximate to the metal container production line (e.g., on the necker out-feeder star wheel 400 which is rotating in a direction of rotation 1301). The feature-detecting imaging apparatus is adapted to detect and determine at least one characteristic feature (e.g., a body maker identifier or a color of a color dot) applied on bottom surfaces of metal containers, one metal container at a time, as each metal container passes by the feature-detecting imaging apparatus on the metal container production line.

The system 1300 also includes at least one defect-detecting imaging apparatus (e.g., 1350 and/or 1360) mounted downstream (i.e., in the direction of travel of the metal containers) from the feature-detecting imaging apparatus on the metal container production line. The defect-detecting imaging apparatus is adapted to detect at least one type of defect (e.g., a dent or crimp in the inside of a metal container) occurring in the metal containers, one metal container at a time, and generate corresponding inspection information as each metal container passes by the defect-detecting imaging apparatus on the metal container production line. In accordance with an embodiment of the present invention, the apparatus 1350 looks for defects in the body inside of a metal container, whereas the apparatus 1360 looks for defects in the neck of the metal container. The resultant inspection information may include simple pass/fail information or quality level information. Other inspection imaging apparatus are possible as well.

Each imaging apparatus (feature-detecting or defect-detecting) has its own part-identification code. A part-identification code of each imaging apparatus may be modified (e.g., incremented or decremented) to generate a part-identification value, in accordance with an embodiment of the present invention.

The system 1300 further comprises a controller 1310 operationally interfacing to the feature-detecting imaging apparatus (e.g., 100 or 700, and/or 1000) and the defect-detecting imaging apparatus (e.g., 1350 and/or 1360). The controller 1310 is adapted to trigger the feature-detecting imaging apparatus and the defect-detecting imaging apparatus to acquire images and to modify a part-identification code in response to any of the feature-detecting imaging apparatus or the defect-detecting imaging apparatus being triggered. The controller 1310 comprises a processor-based device, in accordance with an embodiment of the present invention (e.g., a PC or a programmable logic controller (PLC)).

In accordance with an embodiment of the present invention, modifying a part-identification code includes incrementing a numerical value by one to generate a part-identification value every time the controller 1310 attempts to trigger the feature-detecting imaging apparatus or the defect-detecting imaging apparatus. Each imaging apparatus has its own part-identification code associated with it. Therefore, when the body maker imaging apparatus 100 is triggered, its corresponding part-identification code is incremented to generate a part-identification value. Similarly, when the neck-inspection imaging apparatus 1360 is triggered, its corresponding part-identification code is incremented to generate a part-identification value. As a result, the part-identification values may be used to synchronize the system 1300. That is, matching part-identification values will correspond to the same metal container, as long as no intervening event has occurred which causes the system to go out of synchronization (e.g., a metal container falling off the production line).

The system 1300 also comprises a correlator 1330 operationally interfacing to the feature detecting imaging apparatus (e.g., 100 or 700, and/or 1000) and the defect-detecting imaging apparatus (e.g., 1350 and/or 1360). The correlator 1330 is adapted to receive at least one determined characteristic feature and inspection information and correlate the received characteristic feature (e.g., a body maker identifier and/or a color dot) and the received inspection information to a particular metal container in response to the part-identification values. As a result, information associated with the same part-identification value may be correlated to the same metal container. The correlator 1330 comprises a processor-based device, in accordance with an embodiment of the present invention (e.g., a PC or a programmable logic controller (PLC)). The controller 1310 and the correlator 1330 may be implemented as separate computer-based devices, for example, or as a single programmable computer-based device 1305 such as a personal computer (PC).

Again, the feature-detecting imaging apparatus may include the apparatus 100 of FIG. 1, for example, or the apparatus 700 of FIG. 7, for example in order to determine the embossed body maker identifier on the bottom surfaces of the metal containers which correlate to particular body maker machines of the metal container production line. The feature-detecting imaging apparatus may also include the apparatus 1000 of FIG. 10, for example, in order to determine the color of a color attribute (e.g., a color dot) on the bottom surfaces of metal containers which correlate to particular spray guns of the metal container production line. The feature-detecting imaging apparatus 1000 may also determine whether or not an acceptable amount of UV-sensitive coating has been applied to a rim of the bottom surfaces of the metal containers.

The feature-detecting imaging apparatus may further include an image processing device 1320 adapted to process images captured by the camera of the feature-detecting device (100, 700, or 1000) in order to determine the characteristic feature(s). The image processing device 1320, the controller 1310, and the correlator 1330 may be implemented as separate computer-based devices, for example, or as a single programmable computer-based device 1305 such as a personal computer (PC).

In accordance with an embodiment of the present invention, the defect-detecting imaging apparatus 1350 may include a camera, a lens, a source of illumination, and an image processing device adapted to process images captured by the camera for determining any interior type defects and generating corresponding inspection information. Similarly, the defect-detecting imaging apparatus 1360 may include a camera, a lens, a source of illumination, and an image processing device adapted to process images captured by the camera for determining any neck type defects and generating corresponding inspection information. Such defect-detecting imaging apparatus are well-known in the art.

The image processing device for the defect-detecting imaging apparatus (1350 and/or 1360) may be the image processing device 1320, for example, which is shared with the feature-detecting imaging apparatus (100, 700, or 1000). Alternatively, the image processing device for the defect-detecting imaging apparatus (1350 and/or 1360) may be a separate processing device that is dedicated to the defect-detecting imaging apparatus.

The system 1300 further includes an encoder 1340 operationally interfacing to a necker out-feeder star wheel 400 of the metal container production line. The encoder 1340 is adapted to generate an index pulse for every revolution of the star wheel 400 and a plurality of electric encoder pulses over the course of every revolution of the star wheel. The index pulse resets the encoder position in the tracking device at the beginning of a revolution, and the encoder pulses indicate the position of the star wheel during any given revolution. As a result, the system 1300 may be calibrated, using the encoder 1340, to "know" when a current pocket of the star wheel 400 is aligned with a feature-detecting imaging apparatus (e.g., 100). When alignment occurs, the apparatus 100 may be triggered by the controller 1310 to capture an image of the bottom surface of a corresponding metal container in the pocket.

The encoder 1340 operationally interfaces with a tracking device 1370, which is also a part of the system 1300. The tracking device 1370 is adapted to generate a necker pocket identifier corresponding to a current pocket of the necker out-feeder star wheel in response to the index pulse and the encoder pulses, and to generate a part-identification value in response to the necker pocket identifier being generated. That is, the necker out-feeder star wheel may have its own part-identification code as well. As a result, a necker pocket may be correlated to a metal container by way of matching part-identification values. That is, correlator 1330 is further adapted to receive the necker pocket identifier and correlate the received necker pocket identifier to a particular metal container in response to the value of the part-identification code. Alternatively, when the feature-detecting imaging apparatus (e.g., 100) is triggered to acquire an image, the part-identification value that is generated for that acquisition is associated with the current necker pocket identifier. The image processing device 1320, the controller 1310, the correlator 1330, and the tracking device 1370 may be implemented as separate computer-based devices, for example, or as a single programmable computer-based device 1305 such as a personal computer (PC) or a programmable logic device (PLC), for example.

The system 1300 may further include a sensor 1390 mounted proximate to the out-feeder star wheel 400. The sensor 1390 operationally interfaces to the controller 1310 and is adapted to detect a presence (or absence) of a metal container in a current pocket of the star wheel. A part-identification code may be modified in response to the sensor 1390 detecting an absence of a metal container in the current pocket of the star wheel 400 when the feature-detecting imaging apparatus fails to acquire an image for that same current pocket. For example, the part-identification code, that is incremented when the body maker identifier imaging apparatus 100 is triggered, may be decremented if the sensor 1380 determines that there was no metal container present in that current pocket. This helps prevent the system 1300 from going out of synchronization, as will be explained in more detail later herein.

However, under normal conditions, the feature-detecting imaging apparatus (e.g., 100) is further adapted to determine if a metal container is missing from the metal container production line as the metal containers pass by the feature-detecting imaging apparatus on the metal container production line. If a metal container is determined to be missing in a current pocket of the star wheel, for example, the corresponding part-identification code may be decremented by the controller 1310 to account for the missing container, thereby preventing the system 1300 from going out of synchronization.

As part of a re-synchronization process, the controller 1310 is further adapted to reset the part-identification codes, associated with all the imaging apparatus and/or out-feeder star wheel, to an initial value in response to the feature-detecting imaging apparatus determining that a consecutive number of metal containers are missing from the metal container production line. Such a re-synchronization process is explained later herein in more detail with respect to the methods implemented using the system 1300.

Figure 14:
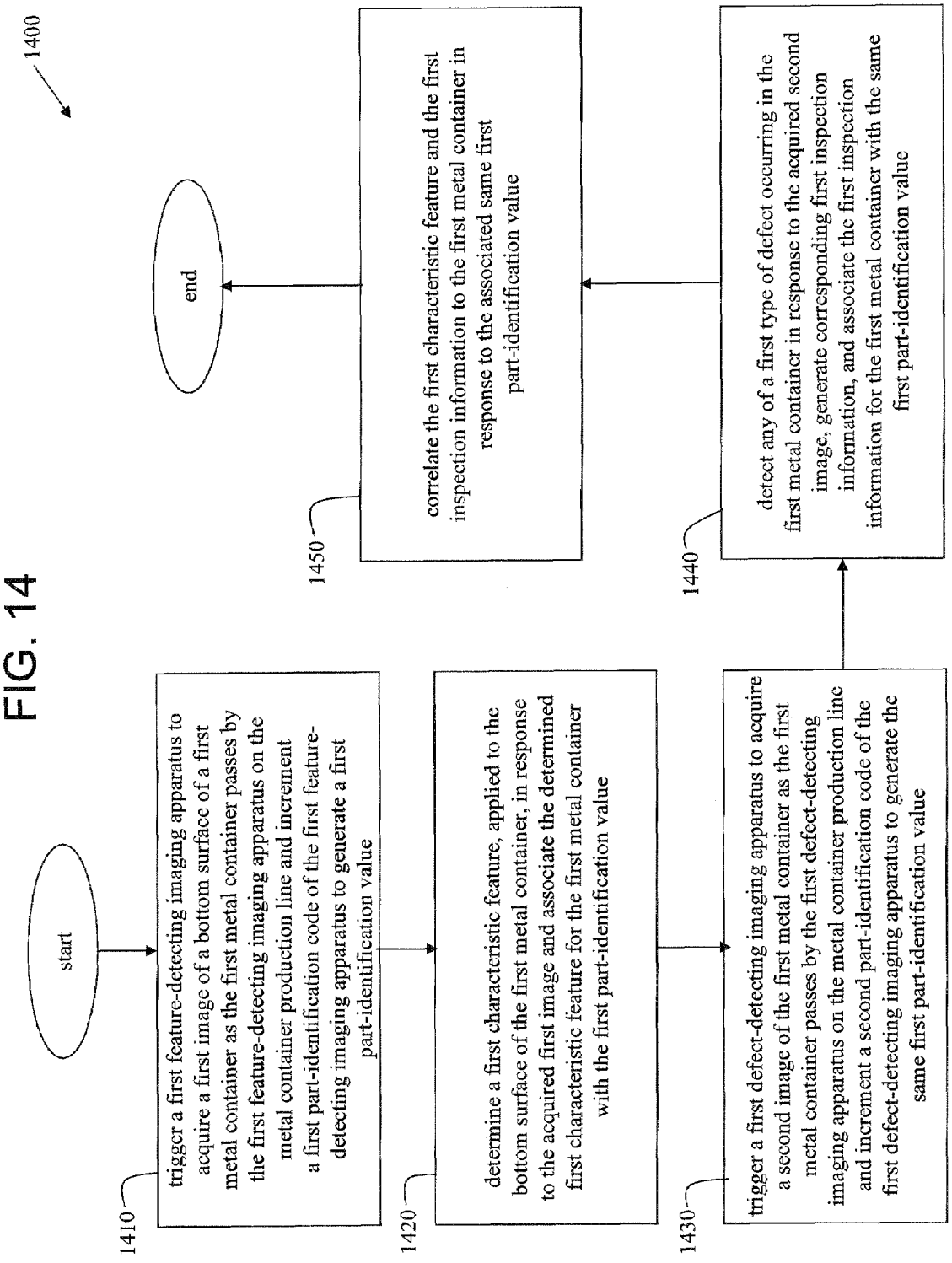
FIG. 14 is a flow chart of a first exemplary embodiment of at least a portion of a method of associating a defective metal container produced on a metal container production line with particular production equipment of the metal container production line using at least a portion of the system of FIG. 13.

FIG. 14 is a flow chart of a first exemplary embodiment of at least a portion of a method 1400 of associating a defective metal container produced on a metal container production line with particular production equipment of the metal container production line using at least a portion of the system 1300 of FIG. 13. In step 1410, trigger a first feature-detecting imaging apparatus to acquire a first image of a bottom surface of a first metal container as the first metal container passes by the first feature-detecting imaging apparatus on the metal container production line, and increment a first part-identification code of the first feature-detecting imaging apparatus to generate a first part-identification value. In step 1420, determine a first characteristic feature, applied to the bottom surface of the first metal container, in response to the acquired first image, and associate the determined first characteristic feature for the first metal container with the first part-identification value.

In step 1430, trigger a first defect-detecting imaging apparatus to acquire a second image of the first metal container as the first metal container passes by the first defect-detecting imaging apparatus on the metal container production line, and increment a second part-identification code of the first defect-detecting imaging apparatus to generate the same first part-identification value. In step 1440, detect any of a first type of defect occurring in the first metal container in response to the acquired second image, generate corresponding first inspection information, and associate the first inspection information for the first metal container with the same first part-identification value. In step 1450, correlate the first characteristic feature and the first inspection information to the first metal container in response to the associated same first part-identification value. The method 1400 is performed automatically and on-line in real time as the metal container production line is manufacturing metal containers.

As an example, referring to FIG. 13, a first metal container on the necker out-feeder star wheel 400 becomes aligned with the body maker identifier imaging apparatus 100 such that the apparatus 100 is triggered by the controller 1310 to acquire a first image of the bottom surface of the first metal container. The part-identification code associated with the apparatus 100 is incremented within the controller 1310 from a value of "0000" to a value of "0001". The image processing device 1320 receives the acquired first image and determines a body maker identifier having a numeric value of "52" from the image. As the first metal container progresses around the out-feeder star wheel 400 and onto the conveyor belt 1380, the first metal container encounters the interior inspection imaging apparatus 1350 such that the apparatus 1350 is triggered by the controller 1310 to acquire a second image of the interior of the first metal container. The part-identification code associated with the apparatus 1350 is incremented within the controller 1310 from a value of "0000" to a value of "0001". The image processing device 1320 receives the acquired second image and generates corresponding inspection information (e.g., a "fail" condition). The correlator 1330 then receives the inspection information and the body maker identifier from the image processing device 1320, each tagged with the same part-identification value of "0001", and correlates the inspection information (of a "fail" condition) and the body maker identifier (of "52") to the same first metal container. As a result, the system now "knows" which body maker machine (based on the correlated body maker identifier) created the defect resulting in the "fail" condition. The "fail" condition may be added to a set of statistics being gathered for the metal container production line and the statistics may be displayed. In this way, an operator may view the displayed statistics as the metal container production line continues to run and gather statistics for other metal containers and determine if a particular machine or machines are causing an unacceptable number of defects. In general, correlated information for the metal containers may be accumulated into statistical data and displayed to an operator on a display in order to determine which specific production equipment on the metal container production line are introducing defects into the metal containers.

The method 1400 may further include generating a first necker pocket identifier corresponding to a current pocket of a necker out-feeder star wheel holding the first metal container and associating the first necker pocket identifier for the first metal container with the first part-identification value; and correlating the first characteristic feature, the first inspection information, and the first necker pocket identifier to the first metal container in response to the associated same first part-identification value.

Continuing with the example, when the body maker identifier imaging apparatus 100 is triggered by the controller 1310, the controller 1310 captures the decoded necker pocket identifier (e.g., having a numeric value of "9") which is generated by the tracking device 1370 in response to the encoder pulses from the encoder 1340. The system 1300 is configured and calibrated such that the captured necker pocket identifier corresponds to the current necker pocket holding the first metal container over the imaging apparatus 100. As a result, the captured necker pocket identifier is associated with the incremented part-identification value for the imaging apparatus 100. Alternatively, the necker out-feeder star wheel 400 may have its own part-identification code associated with it in the controller 1310 or tracking device 1370 and which is incremented to a value of "0001" when the necker pocket identifier is captured by the controller 1310. The correlator 1330 may then correlate the body maker identifier of "52", the inspection "fail" condition, and the necker pocket number "9" to the first metal container based on the "common" first part-identification value of "0001".

The method 1400 may further include triggering a second feature-detecting imaging apparatus to acquire a third image of the bottom surface of the first metal container as the first metal container passes by the second feature-detecting imaging apparatus on the metal container production line, and incrementing a third part-identification code of the second feature-detecting imaging apparatus to generate the same first part identification value; determining a second characteristic feature, applied to the bottom surface of the first metal container, in response to the acquired third image, and associating the determined second characteristic feature for the first metal container with the same first part-identification value; and correlating the first characteristic feature, the second characteristic feature, the first necker pocket identifier, and the first inspection information to the first metal container in response to the associated same first part-identification value.

Continuing with the example, the second feature-detecting imaging apparatus may comprise the color-dot/UV imaging apparatus 1000 for detecting color attributes and is mounted on or proximate to the necker out-feeder star wheel 400. Referring to FIG. 13, the imaging apparatus 1000 is triggered when the first metal container becomes substantially aligned with the apparatus 1000 and acquires a third image of the bottom surface of the first metal container. This third image is actually acquired in time before the second image, previously discussed, is acquired by the first defect-detecting imaging apparatus 1350 since the apparatus 1000 is upstream from the apparatus 1350. The apparatus 1000 has its own part-identification code associated with it which gets incremented from a value of "0000" to "0001" when the apparatus 1000 acquires the third image.

The image processing device 1320 processes the acquired third image and determines, for example, that a color dot on the bottom surface of the first metal container is substantially "blue" and was, therefore, sprayed by a particular sprayer gun. As before, because of the "common" part-identification value of "0001", the correlator 1330 may correlate the first characteristic feature "52", the second characteristic feature "blue", the necker pocket number "9", and the first inspection information "fail" to the first metal container in response to the associated same first part-identification value "0001". Furthermore, the image processing device 1320 may determine that a UV-sensitive rim coating on the rim of the bottom surface of the first metal container is insufficient (i.e., a "fail" condition on the rim coating). The condition of the insufficient rim coating will also be associated with the part-identification value of "0001" and, therefore, correlated to the first metal container.

The method 1400 may further include triggering a second defect-detecting imaging apparatus to acquire a fourth image of the first metal container as the first metal container passes by the second defect-detecting imaging apparatus on the metal container production line, and incrementing a fourth part-identification code of the second defect-detecting imaging apparatus to generate the same first part-identification value; detecting any of a second type of defect occurring in the first metal container in response to the acquired fourth image, generating corresponding second inspection information, and associating the second inspection information for the first metal container with the same first part-identification value; and correlating the first characteristic feature, the second characteristic feature, the first inspection information, the second inspection information, and the first necker pocket identifier to the first metal container in response to the associated same first part-identification value.

Continuing with the example, as the first metal container progresses on the metal container production line and becomes substantially aligned with the neck inspection imaging apparatus 1360, the apparatus 1360 is triggered by the controller 1310 to acquire a fourth image of the neck region of the first metal container. The part-identification code associated with the apparatus 1360 is incremented within the controller 1310 from a value of "0000" to a value of "0001". The image processing device 1320 receives the acquired fourth image and generates corresponding second inspection information (e.g., a "pass" condition). The correlator 1330 receives the second inspection information "pass", the first inspection information "fail", the body maker identifier "52", the color dot information "blue", and the necker pocket number "9" from the image processing device 1320, each tagged with the same part-identification value of "0001", and correlates all of these to the same first metal container. As a result, the system has determined a body maker identifier, a color dot, any interior defects, any neck defects, as well as a necker pocket for the first metal container because each of these results are associated with a same part-identification value. If a defect in the neck of the first metal container had been detected by the defect-detecting imaging apparatus 1360, the system 1300 would "know" that it was necker pocket number "9" of the out-feeder star wheel 400 and, therefore, of all the star wheels, which produced the defect, since any given metal container is processed through the same pocket number on all the necker star wheels of the metal container production line.

Similarly, the method 1400 may be repeated for subsequent metal containers coming after the first metal container on the metal container production line. That is, a second metal container, a third metal container, a fourth metal container, etc. For example, when a next (i.e., second) metal container encounters any of the feature detecting imaging apparatus (e.g., 100, 700, or 1000 for example in pocket number "10" of the out-feeder star wheel), and any of the defect-detecting imaging apparatus (e.g., 1350, 1360), each corresponding part-identification code for the particular imaging apparatus will be incremented from a first part-identification value of "0001" to a second part-identification value of "0002" indicating that the acquired images correspond to a second metal container. Therefore, any features, inspection information, and necker pocket identifier determined for the second metal container will be correlated to the second metal container based on the "common" part-identification value "0002".

If, however, the feature-detecting imaging apparatus (e.g., 100) does not detect a second metal container in pocket number "10" in response to the acquired image, then the part-identification code for the apparatus 100 is decremented from a value of "0002" to a value of "0001" in order to keep the system 1300 in synchronization. Also, if the feature-detecting imaging apparatus (e.g., 100) fails to trigger and acquire an image (even though its part-identification code has been incremented to a value of "0002"), and the sensor 1390 detects that a metal container is missing from pocket number "10", then the part-identification code for the apparatus 100 is decremented from a value of "0002" to a value of "0001" in order to keep the system 1300 in synchronization.

If a metal container on a metal container production line is imaged by a feature-detecting imaging apparatus (e.g., 100, 700, or 1000) and the metal container unintentionally falls off the line or is intentionally pulled off the line before the metal container reaches a defect-detecting imaging apparatus (e.g., 1350 or 1360), then the system 1300 will go out of synchronization. That is, the part-identification numbers will no longer correlate to the correct metal containers between the feature-detecting imaging apparatus and the defect-detecting imaging apparatus.

When the system 1300 goes out of synchronization, a re-synchronization signal or command may be generated to initiate re-synchronization of the system 1300. For example, an operator may press a button or select a re-sync icon on a display to initiate re-synchronization. When the re-synchronization signal or command is generated, a pre-determined number (e.g. "64") of contiguous metal container positions from a portion of the metal container production line are automatically un-populated (i.e., no metal containers in those positions) in response to the re-synchronization signal or command. Furthermore, all part-identification codes are reset to the same initial part-identification code (e.g., "0000") in response to the un-populated pre-determined number of contiguous metal container positions traveling through the metal container production line. In accordance with an embodiment of the present invention, the first feature-detecting imaging apparatus (e.g., 100) determines when the un-populated pre-determined number of contiguous metal container positions have passed through the metal container production line. Subsequently, metal containers traveling on the metal container production line will be processed once again in synchronization such that proper correlation may be performed as described herein.

As an alternative or in addition, re-synchronization may be initiated when at least a pre-determined number (e.g., "64") of contiguous un-populated metal container positions from a portion of the metal container production line are detected or determined by, for example, the first feature-detecting imaging apparatus (e.g., 100). In other words, no separate initiation of re-synchronization is performed by an operator. The fact that at least a pre-determined number of contiguous un-populated metal container positions are detected is enough to initiate re-synchronization. There are often times on a metal container production line when, for one reason or another, at least a certain number of metal containers are missing from the production line. Therefore, re-synchronization may be initiated simply by the determination that the containers are missing. In such a re-synchronization process, after determination of the missing containers, all part-identification codes are reset to the same initial part-identification code (e.g., "0000") in response to the un-populated pre-determined number of contiguous metal container positions, or more, traveling through the metal container production line.

In accordance with various embodiments of the present invention, various imaging apparatus may be present or absent from the system 1300. For example, the system may include no feature-detecting imaging apparatus and only one defect-detecting imaging apparatus (e.g., the necker imaging apparatus 1360). As a result, inspection information from the defect-detecting imaging apparatus is correlated to a necker pocket for a particular metal container. Methods of using such an exemplary system are described herein below.

Figure 15:
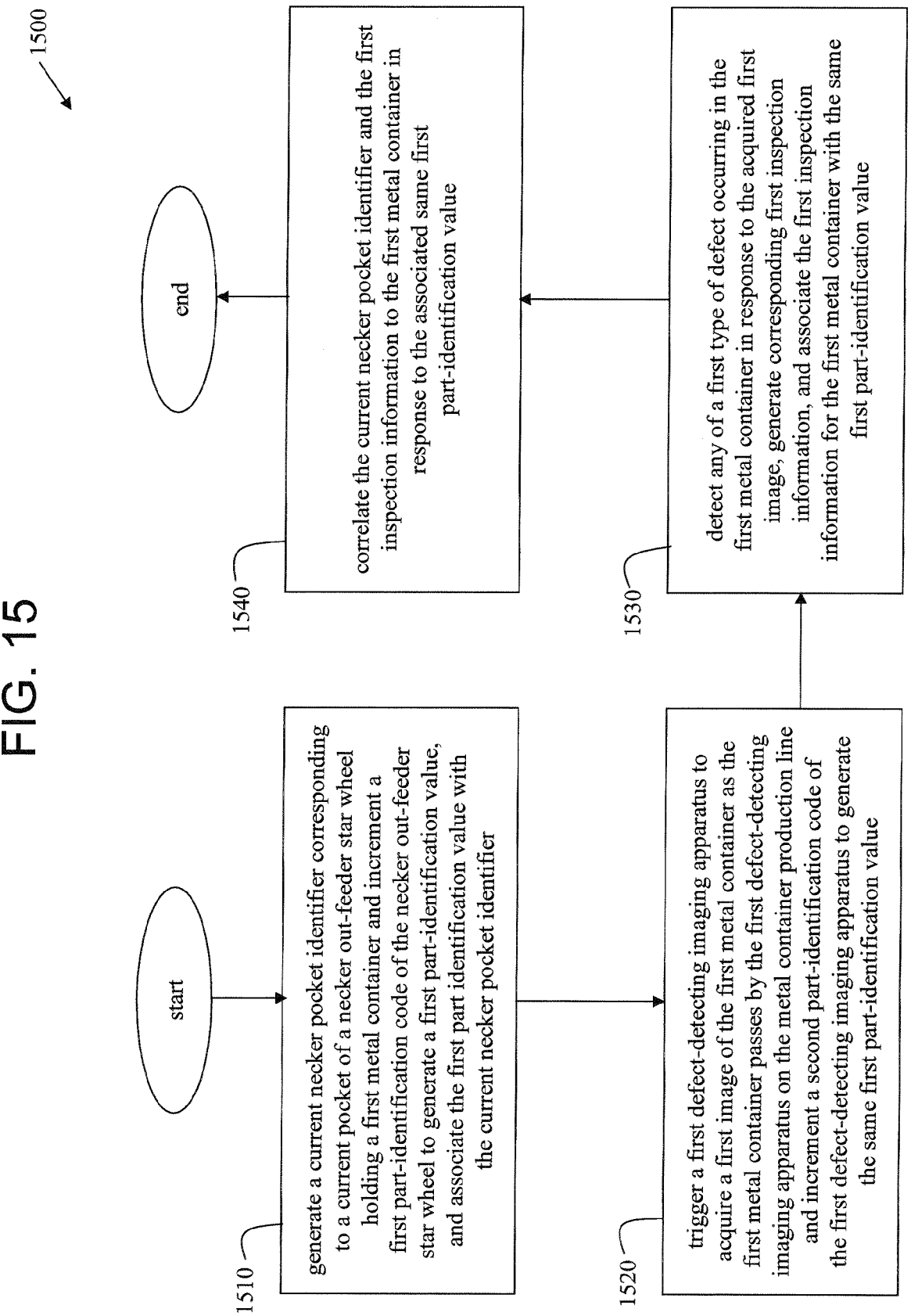
FIG. 15 is a flow chart of a second exemplary embodiment of at least a portion of a method of associating a defective metal container produced on a metal container production line with particular production equipment of the metal container production line using at least a portion of the system of FIG. 13.

FIG. 15 is a flow chart of a second exemplary embodiment of at least a portion of a method 1500 of associating a defective metal container produced on a metal container production line with particular production equipment of the metal container production line using at least a portion of the system 1300 of FIG. 13. In step 1510, generate a current necker pocket identifier corresponding to a current pocket of a necker out-feeder star wheel holding a first metal container and increment a first part-identification code of the necker out-feeder star wheel to generate a first part-identification value, and associate the first part identification value with the current necker pocket identifier. In step 1520, trigger a first defect-detecting imaging apparatus to acquire a first image of the first metal container as the first metal container passes by the first defect-detecting imaging apparatus on the metal container production line, and increment a second part-identification code of the first defect-detecting imaging apparatus to generate the same first part-identification value.

In step 1530, detect any of a first type of defect occurring in the first metal container in response to the acquired first image, generate corresponding first inspection information, and associate the first inspection information for the first metal container with the same first part-identification value. In step 1540, correlate the current necker pocket identifier and the first inspection information to the first metal container in response to the associated same first part-identification value. The method 1500 is performed automatically and on-line in real time as the metal container production line is manufacturing metal containers.

For example, referring to FIG. 13, only one imaging apparatus (e.g., 1360) may be present in an embodiment for detecting neck defects. The controller 1310 captures the decoded necker pocket identifier (e.g., having a numeric value of "15") which is generated by the tracking device 1370 in response to the encoder pulses from the encoder 1340. When the necker pocket identifier is captured, its corresponding part-identification code is incremented by the controller 1310 from a part-identification value of "0000" to a part-identification value of "0001". The system 1300 is configured and calibrated such that the captured necker pocket identifier corresponds to the necker pocket holding the first metal container in the necker out-feeder star wheel 400. As a result, the captured necker pocket identifier is associated with the incremented part-identification value "0001" for the star wheel 400.

When the first metal container reaches the defect-imaging apparatus 1360 (neck inspection apparatus), a first image is acquired and the part-identification code of the apparatus 1360 is incremented from a value of "0000" to a value of "0001". The image processing device 1320 processes the first acquired image and generates first inspection information corresponding to, for example, a defect (a "fail" condition) in the first metal container. Again, the inspection information may include pass/fail information and/or quality information. An example of quality information is a size of the defect.

The correlator 1330 may then correlate the first inspection result (e.g., "fail") and the necker pocket number "15" to the first metal container based on the "common" first part-identification value of "0001". As a result, the system 1300, having only one imaging apparatus 1360, "knows" which necker pocket of the necker star wheels is responsible for creating the defect in the first metal container.

In another embodiment, the system may include both the defect-detecting imaging apparatus 1360 and the defect-detecting imaging apparatus 1350, but no feature-detecting imaging apparatus on the out-feeder star wheel 400. As a result, first inspection information, second inspection information, and necker pocket may be correlated to the first metal container based on the "common" part-identification value using the synchronization processes described herein. Similarly, the method 1500 may be repeated for subsequent metal containers coming after the first metal container on the metal container production line. That is, a second metal container, a third metal container, a fourth metal container, etc.

Again, if a metal container is intentionally or unintentionally eliminated from the production line (e.g., the out-feeder star wheel or the first part of the conveyor 1380) before reaching a defect-detecting imaging apparatus and causing the system 1300 to go out of synchronization, the re-synchronization process may be initiated. Again, a pre-determined number of contiguous metal container positions are un-populated on the metal container production line in response to a generated re-synchronization signal and all part-identification codes are reset when the pre-determined number of contiguous un-populated metal container positions pass through the metal container production line. However, in embodiments where there is no feature-detecting imaging apparatus (e.g., 100) on or adjacent to the out-feeder star wheel 400, the sensor 1390 determines when the un-populated pre-determined number of contiguous metal container positions have passed through the metal container production line. Subsequently, metal containers traveling on the metal container production line will be processed once again in synchronization such that proper correlation may be performed as described herein.

Again, correlated information for the metal containers may be accumulated into statistical data and displayed to an operator on a display in order to determine which specific production equipment on the metal container production line are introducing defects into the metal containers.

In summary, apparatus, systems, and methods to recognize features on bottom surfaces of metal containers on a metal container production line, detect defects in the metal containers, and correlate the defects to specific production equipment of the metal container production line, based in part on the recognized features, are disclosed. Imaging apparatus along with tracking and synchronization techniques for accomplishing such correlation are described.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. An apparatus for imaging at least one color attribute of each of a plurality of metal containers, one at a time, as each said container passes by said apparatus on a metal container production line, said apparatus comprising:
   a color camera having an optical aperture;
   a lens having a central optical axis and a capture angle and being operationally attached to said color camera to provide light to said optical aperture of said color camera; and
   a binary source of illumination arranged substantially circumferentially around said central optical axis of said lens and capable of providing simultaneous illumination of substantially white light and ultraviolet light.

2. The apparatus of claim 1 wherein said binary source of illumination comprises an away of substantially white light-emitting diodes (LEDs) and ultraviolet LEDs arranged in a plane around said central optical axis of said lens.

3. The apparatus of claim 2 wherein said array of substantially white LEDs are arranged in three concentric rings around said central optical axis.

4. The apparatus of claim 3 wherein said ultraviolet LEDs are arranged substantially in a concentric ring around said substantially white LEDs.

5. The apparatus of claim 4 further comprising a substantially tubular separator positioned concentrically between said substantially white LEDs and said ultraviolet LEDs.

6. The apparatus of claim 5 wherein an inner surface of said separator faces said substantially white LEDS and is substantially white, and wherein an outer surface of said separator faces said ultraviolet LEDs and is substantially silver.

7. The apparatus of claim 2 further comprising a circuit board onto which said array of LEDs is mounted.

8. The apparatus of claim 1 wherein said capture angle of said lens is at least 60 degrees.

9. The apparatus of claim 1 further comprising a controller operationally interfacing to said color camera and/or said binary source of illumination such that said controller is adapted to electronically trigger said color camera and/or said binary source of illumination to capture images.

10. The apparatus of claim 9 wherein said controller is synchronized to a rotation of an out-feeder star wheel of said metal container production line such that said color camera and/or said binary source of illumination is electronically triggered by said controller when a pocket of said out-feeder star wheel adapted to hold one of said plurality of metal containers is substantially aligned with said central optical axis of said lens.

11. The apparatus of claim 1 further comprising a mounting structure allowing mounting of said color camera, said lens, and said binary source of illumination onto an out-feeder star wheel of said metal container production line such that said apparatus is capable of imaging a bottom surface of each of said plurality of metal containers, one at a time, as each said container passes above said apparatus on said out-feeder star wheel.

12. The apparatus of claim 1 further comprising a diffuser window located adjacent said lens and said source of illumination and adapted to substantially diffuse said white light from said binary source of illumination.

13. The apparatus of claim 12 further comprising a substantially transparent window adjacent said diffuser window and adapted to protect said diffuser window, said lens, and said binary source of illumination.

14. The apparatus of claim 1 further comprising an image processing device adapted to process images acquired by said color camera.

15. A method of recognizing at least one color attribute on a bottom surface of a metal container traveling on a metal container production line, said method comprising:
  acquiring a color image of a bottom surface of a metal container, having at least one color attribute, as said metal container passes by a color imaging apparatus on a metal container production line;
  color balancing a pre-defined region-of-interest (ROI) of said color image to eliminate any unwanted color hue from said ROI and to provide a uniform brightness from metal container to metal container;
  generating a distance value for each of a first set of pixels within said ROI to determine how different from each other are at least two color components of each of said first set of pixels;
  associating pixels within said ROI, having a distance value greater than a pre-defined distance threshold value, with said color attribute;
  generating an average color value of said associated pixels using corresponding color pixels in said color image; and
  estimating a color of said color attribute in response to said average color value using a color discrimination tool.

16. The method of claim 15 further comprising associating said metal container with a particular spray gun in response to said estimated color.

17. The method of claim 16 wherein said step of associating said metal container with a particular spray gun in response to said estimated color includes determining which cluster in a color space, of a plurality of clusters in said color space corresponding to a plurality of spray guns, is closest, in said color space, to said estimated color.

18. The method of claim 17 wherein said color space comprises a domain of color hue and color saturation.

19. The method of claim 17 wherein each cluster of said plurality of clusters includes a pre-defined centroid in said color space derived from estimated colors corresponding to said spray guns.

20. The method of claim 15 further comprising correlating said estimated color of said color attribute to a pocket of an out-feeder star wheel of said metal container production line adapted to hold said metal container.

21. The method of claim 15 further comprising:
  determining at least two spatial parameters of said imaged bottom surface in response to said acquired color image; and
  scaling said acquired color image in response to said determined at least two spatial parameters.

22. The method of claim 21 wherein said at least two spatial parameters include a center location and a radius of said imaged bottom surface.

23. The method of claim 21 wherein said step of determining said at least two spatial parameters of said imaged bottom surface from said acquired color image includes converting said acquired color image to a monochrome image.

24. The method of claim 15 further comprising:
  determining a number NB of a second set of pixels within said color image that are outside of said pre-defined ROI and having a blue color component value that is greater than a pre-defined blue threshold value; and
  comparing said number NB to a pre-defined rim coat test threshold value RCT.

25. The method of claim 24 further comprising generating a "fail" condition if said number NB is less than said rim coat test threshold value RCT.

26. The method of claim 15 further comprising simultaneously illuminating a first portion of said bottom surface of said metal container with substantially white light and a second portion of said bottom surface with ultraviolet light as part of said acquiring.

27. The method of claim 15 wherein said step of color balancing comprises measuring average values of red, green, and blue color components of pixels within said ROI and scaling said red, green, and blue color components of each pixel within said ROI in response to said measured average values of red, green and blue color components of said ROI such that an average of each of said red, green, and blue color components of pixels within said ROI become equal to each other.

28. The method of claim 15 wherein said distance value for any pixel having said at least two color components comprising red R, green G, and blue B color components is a function of a quantity defined as $[(R-G)^2+(R-B)^2+(G-B)^2]$.

29. The method of claim 15 further comprising comparing a number N of said associated pixels with a threshold value V such that said associated pixels are not considered to correspond to said color attribute if said number N of said associated pixels is less than said threshold value V.

30. The method of claim 15 further comprising flagging as being black any pixel having each of a red color component R, a green color component G, and a blue color component B being less than a threshold value BL.

31. The method of claim 15 wherein said color discrimination tool is trained from a plurality of estimated color attributes derived from a corresponding plurality of acquired color images that have been processed through at least said color balancing step, said first generating step, said associating step, and said second generating step.

32. The method of claim 15 wherein said at least one color attribute comprises a color dot painted on said bottom surface.

* * * * *